US010563249B2

(12) United States Patent
Yasuda et al.

(10) Patent No.: US 10,563,249 B2
(45) Date of Patent: Feb. 18, 2020

(54) PRIMER SET FOR DETECTION OF ZAIRE EBOLA VIRUS, ASSAY KIT, AND AMPLIFICATION METHOD

(71) Applicants: Nagasaki University, Nagasaki-shi (JP); Toshiba Medical Systems Corporation, Otawara-shi (JP)

(72) Inventors: Jiro Yasuda, Nagasaki (JP); Yohei Kurosaki, Nagasaki (JP)

(73) Assignees: Nagasaki University, Nagasaki-shi (JP); Canon Medical Systems Corporation, Otawara-shi (JP)

( * ) Notice: Subject to any disclaimer, the term of this patent is extended or adjusted under 35 U.S.C. 154(b) by 209 days.

(21) Appl. No.: 15/626,938

(22) Filed: Jun. 19, 2017

(65) Prior Publication Data

US 2017/0369940 A1 Dec. 28, 2017

Related U.S. Application Data

(63) Continuation of application No. PCT/JP2015/085534, filed on Dec. 18, 2015.

(30) Foreign Application Priority Data

Dec. 19, 2014 (JP) ................................ 2014-258074
Jun. 19, 2015 (JP) ................................ 2015-123538

(51) Int. Cl.

*C12Q 1/68* (2018.01)
*C12Q 1/06* (2006.01)
*C12N 15/70* (2006.01)
*C12Q 1/6853* (2018.01)
*C12Q 1/686* (2018.01)
*C12Q 1/6851* (2018.01)

(52) U.S. Cl.

CPC .......... *C12Q 1/6853* (2013.01); *C12N 15/70* (2013.01); *C12Q 1/06* (2013.01); *C12Q 1/686* (2013.01); *C12Q 1/6851* (2013.01); *C12Q 2531/113* (2013.01); *C12Q 2563/107* (2013.01)

(58) Field of Classification Search
CPC ...... C12Q 1/70; C12Q 1/6851; C12Q 1/6853; C12Q 2525/301; C12Q 2563/107
See application file for complete search history.

(56) References Cited

U.S. PATENT DOCUMENTS

| | | | | | |
|---|---|---|---|---|---|
| 7,211,378 | B2 * | 5/2007 | Kawaoka | C07K 14/005 435/5 |
| 2004/0038253 | A1 | 2/2004 | Nagamine | |
| 2018/0340215 | A1 * | 11/2018 | Metsky | C12Q 1/6809 |

FOREIGN PATENT DOCUMENTS

| | | | |
|---|---|---|---|
| EP | 1 327 679 A1 | 7/2003 |
| WO | WO 02/24902 A1 | 3/2002 |

OTHER PUBLICATIONS

International Search Report dated Mar. 22, 2016 in PCT/JP2015/085534, filed on Dec. 18, 2015(with English Translation).
Written Opinion dated Mar. 22, 2016 in PCT/JP2015/085534, filed on Dec. 18, 2015.
Yohei Kurosaki et al., "Rapid and simple detection of Ebola virus by reverse transcription-loop-mediated isothermal amplification", Journal of Virological Methods, vol. 141, No. 1, 2007, pp. 6.
Huan Li et al., "Survey and Visual Detection of Zaire ebolavirus in Clinical Samples Targeting the Nucleoprotein Gene in Sierra Leone", frontiers in Microbiology, vol. 6, Art. 1332,Dec. 2015, pp. 7.
Hiroshi Takano et al., "LAMP(Loop-mediated isothermal amplification) Loop-mediated isothermal amplification (LAMP); Principle and applications", Modern Media, vol. 60, No. 7,Jul. 2014, pp. 21.
Yohei Kurosaki et al., "Clinical evaluation of a rapid detection assay for Ebola virus in Guinea", The 56th Annual Meeting for the Japanese Society of Tropical Medicine—Program and Abstracts, vol. 56, Dec. 2015, pp. 4.

* cited by examiner

*Primary Examiner* — David C Thomas
(74) *Attorney, Agent, or Firm* — Oblon, McClelland, Maier & Neustadt, L.L.P.

(57) ABSTRACT

According to one embodiment, there is provided a nucleic acid primer set that amplifies a ZEBOV gene. An F1 sequence includes at least 13 consecutive bases included in SEQ ID NO: 31 or 64. An F2 sequence includes at least 13 bases included in SEQ ID NO: 62 or 63. An F3 sequence includes at least 13 bases included in SEQ ID NO: 29, 36, 38, 55, 56, 57, 58, 59, 60, 61 or 61. A B1c sequence includes at least 13 bases included in SEQ ID NO: 68, 69, 70, 71, 72, 73, 74 or 75. A B2c sequence includes at least 13 bases included in SEQ ID NO: 65 or 66. A B3c sequence includes at least 13 bases included in SEQ ID NO: 34, 67, 82 or 83.

19 Claims, 16 Drawing Sheets

Specification includes a Sequence Listing.

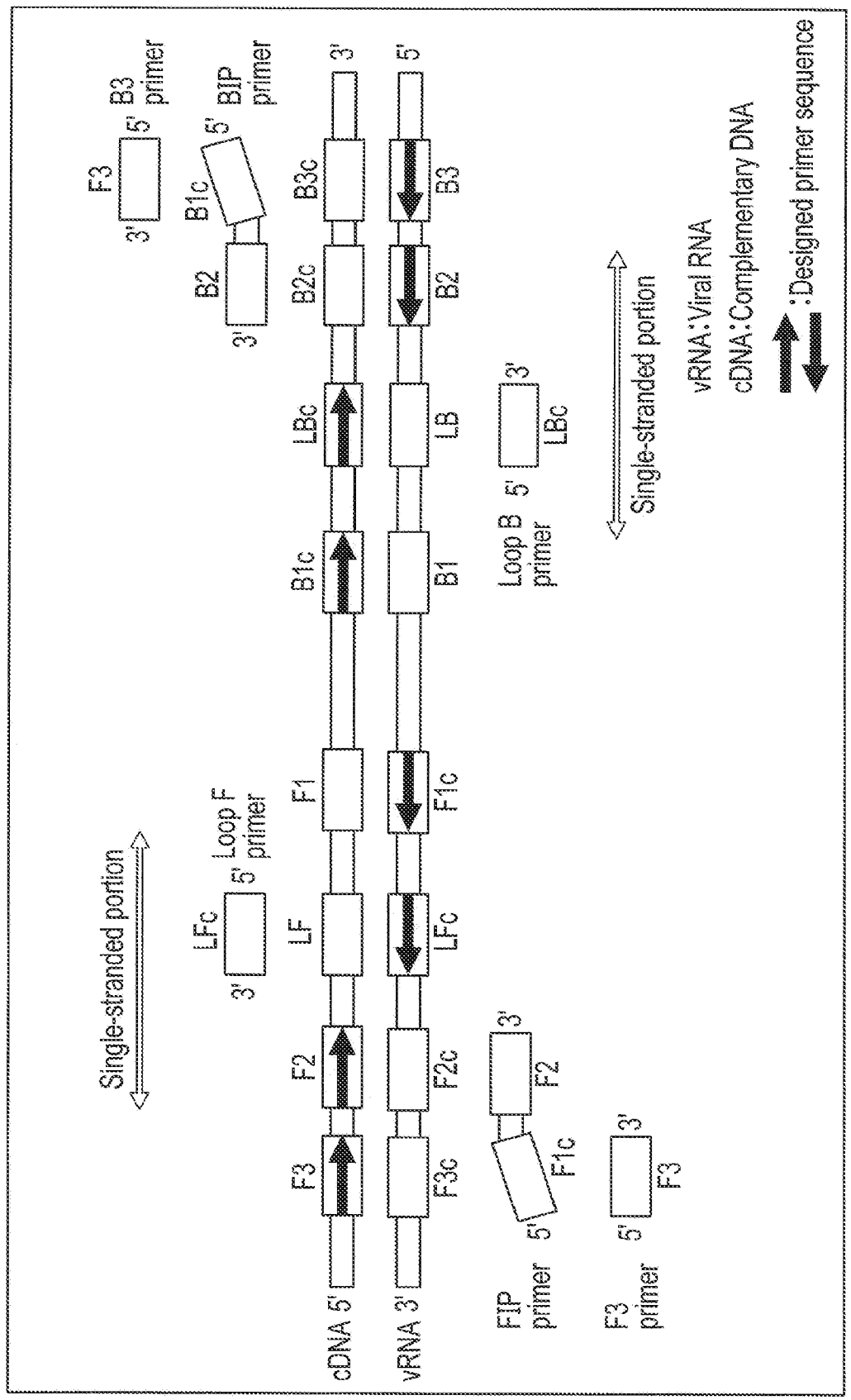
F I G. 1B

FIG. 2C

```
                F1c
         TGTGTGAC (4) (5c)
         TGTGTGACATATT (31)
         TGTGTGAC (44)                                  B1c
         TGTGTGACA (45)
         TGTGTGACATATT (64)
         TGTGTGAC (79)
                                      (91c) (6)  AACGCAACATAATAAACTCTGCA
                                      (92c) (32) GAATTTAACGCAACATAATAAACTCTGCA
                                (93c) (46) GCAATGAGTCTAACGCAACATAATAAACTC
                              (94c) (47) CTGCAATGAGTCTAACGCAAC
                            (95c) (48) GCTGCAATGAGTCTAACGCAA
                            (96c) (49) GCCGCAATGAATTTAACGCAA
                            (97c) (68) GCCGCAATGAATTTAACGCAACATAATAAACTCTGCA
                            (98c) (69) GCTGCAATGAATTTAACGCAACATAATAAACTCTGCA
                            (99c) (70) GCCGCAATGAGTTTAACGCAACATAATAAACTCTGCA
                            (100c) (71) GCCGCAATGAATCTAACGCAACATAATAAACTCTGCA
                            (101c) (72) GCTGCAATGAGTTTAACGCAACATAATAAACTCTGCA
                            (102c) (73) GCCGCAATGAGTCTAACGCAACATAATAAACTCTGCA
                            (103c) (74) CTGCAATGAATCTAACGCAACATAATAAACTCTGCA         LBc
                            (104c) (75) GCTGCAATGAGTCTAACGCAACATAATAAACTCTGCA
                                                                              (28) CTCTTTA
                                                                              (77) CTCTTTA
    121: TGTGTGACATATTACTGCCGCAATGAATTTAACGCAACATAATAAACTCTGCACTCTTTA :180
                                                  B2              B1c
              LBc                   (7)(8c) CTGGGCTCATATTGTTATTGAT
         TAATTAAGCTTTAACG (28)
         TAATTAAGCTTTAA (77)
                              (33) CTGGGCTCATATTGTTATTGAT
                      (86c) (50) GGTCTGGGCTCATATTGT
                     (87c) (51) CGAAAGGTCTGGGCTCAT
                     (88c) (52) CGAAAGGTCTGGGCTCATA
                         (89c) (53) TAGGTCTGGGCTCATATT                        B3
                         (90c) (54) AAGGTCTGGGCTCATATT
                     (65) CGATAGGTCTGGGCTCATATTGTTATTGAT  (9) (10c) TGTTGTATC
                     (66) CGAAAGGTCTGGGCTCATATTGTTATTGAT  (30) (16c) TGTTGTATC
                                   (78) CTGGGCTCATATTGTTATTGA  (34) TGTTGTATC
                                                              (67) TGTTGTATC
                                                         (35c) (82) TGTTGTATC
                                                              (83) TGTTGTATC
    181: TAATTAAGCTTTAACGAAAGGTCTGGGCTCATATTGTTATTGATATAATAATGTTGTATC :240
              B3                                   B2c
         AATATCTTGCCAG (9) (10c)
         AATATCCTGTCAG (16c)
         AATATCCTGTCAGATGGAATAGTGTTTTG (34)
         AATATCTTGTCAGATGGAATAGTGTTTTG (67)
              TCCTGTCAGATGGAATAGTG (19c) (81)
              TCCTGTCAGATGGAATAGTGT (80c)
         AATATCTTGCCAGATGGAATAGTGTTTTG (82)
         AATATCCTGTCAGATGGAATAGTGTTTTG (83) (37c)
    241: AATATCCTGTCAGATGGAATAGTGTTTTGGTTGATAACACAACTTCTTAAAACAAAATTG :300
              B3c
    301: ATCTTTAAGATTAAGTTTTTATAATTATCATTACTTTAATTTGTCGTTTTAAAAACGGT :360
```

FIG. 3B

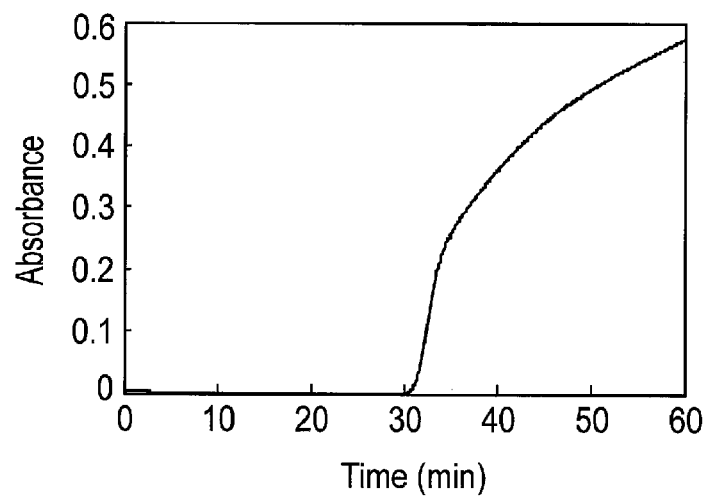
F I G. 5A
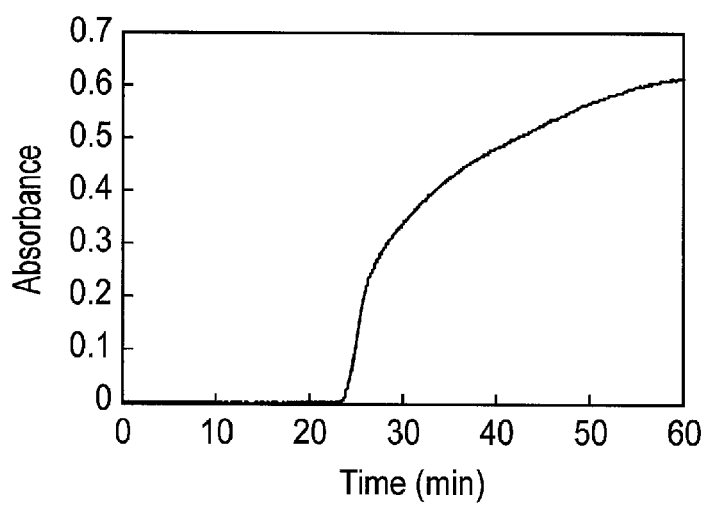
F I G. 5B

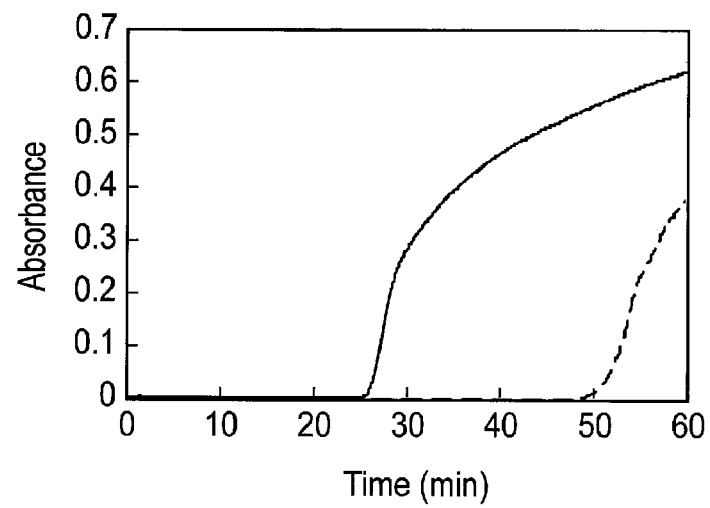
F I G. 5C
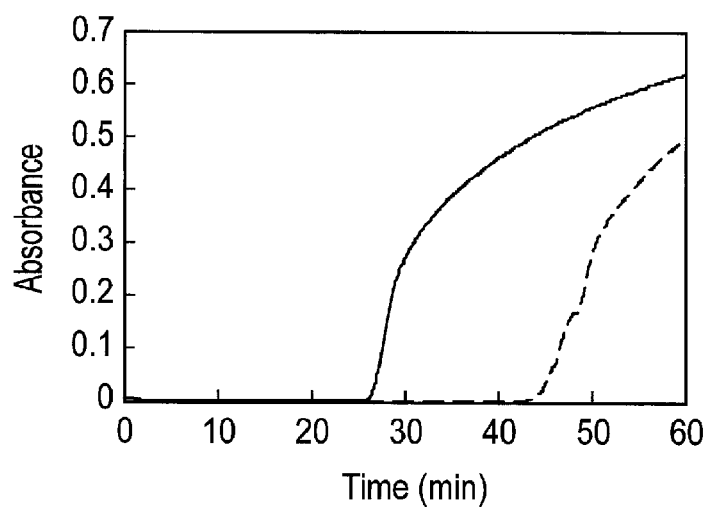
F I G. 5D

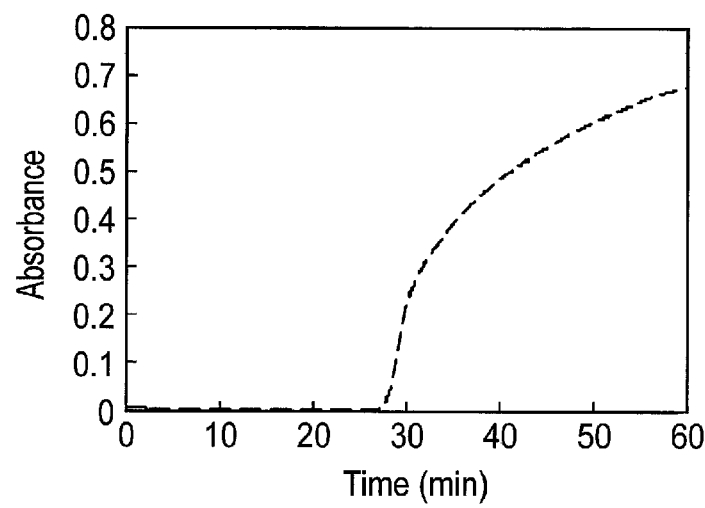
F I G. 5E
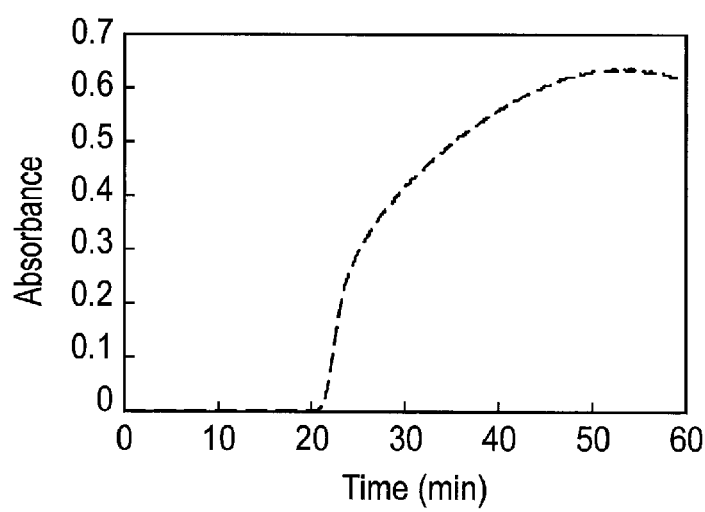
F I G. 5F

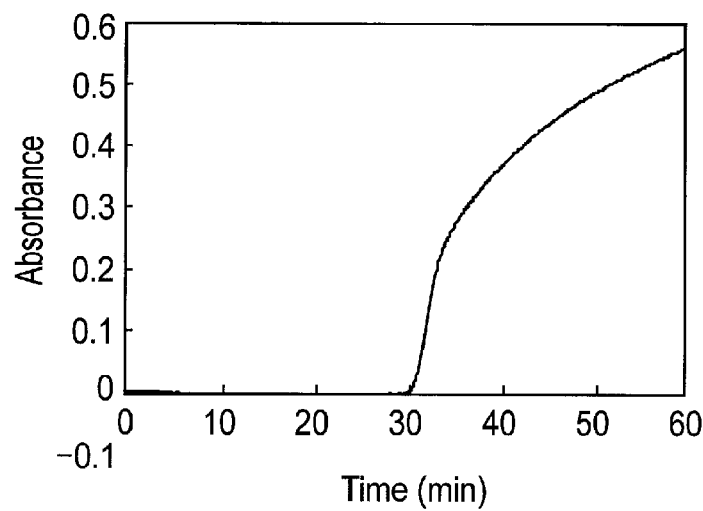
F I G. 5K
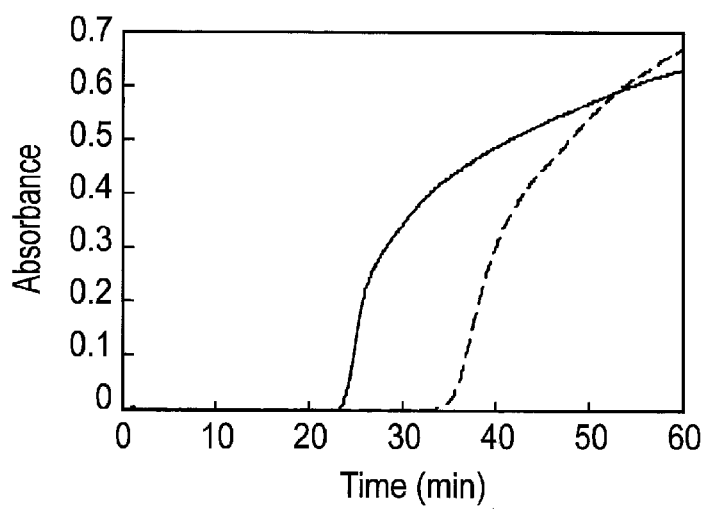
F I G. 5L

SEQUENCE LISTING

<160> NUMBER OF SEQ ID NOS: 104

<210> SEQ ID NO 1
<211> LENGTH: 360
<212> TYPE: DNA
<213> ORGANISM: Artificial Sequence
<220> FEATURE:
<223> OTHER INFORMATION: cDNA of Zaire ebolavirus

<400> SEQUENCE: 1

```
atacatcata ttgatctaat ctcaataaac aactatttaa ataacgaaag gagtccctat      60
attatatact atatttagcc tctctccctg cgtgataatc aaaaaattca caatgcagca     120
tgtgtgacat attactgccg caatgaattt aacgcaacat aataaactct gcactcttta     180
taattaagct ttaacgaaag gtctgggctc atattgttat tgatataata atgttgtatc     240
aatatcctgt cagatggaat agtgttttgg ttgataacac aacttcttaa aacaaaattg     300
atctttaaga ttaagttttt tataattatc attactttaa tttgtcgttt taaaaacggt     360
```

<210> SEQ ID NO 2
<211> LENGTH: 23
<212> TYPE: DNA
<213> ORGANISM: Artificial Sequence
<220> FEATURE:
<223> OTHER INFORMATION: F3 sequence

<400> SEQUENCE: 2

```
caataaacaa ctatttaaat aac                                              23
```

<210> SEQ ID NO 3
<211> LENGTH: 21
<212> TYPE: DNA
<213> ORGANISM: Artificial Sequence
<220> FEATURE:
<223> OTHER INFORMATION: F2 sequence

<400> SEQUENCE: 3

```
ctatatttag cctctctccc t                                                21
```

```
<210> SEQ ID NO 4
<211> LENGTH: 20
<212> TYPE: DNA
<213> ORGANISM: Artificial Sequence
<220> FEATURE:
<223> OTHER INFORMATION: F1 sequence

<400> SEQUENCE: 4
cacaatgcag catgtgtgac                                                 20

<210> SEQ ID NO 5
<211> LENGTH: 20
<212> TYPE: DNA
<213> ORGANISM: Zaire ebolavirus

<400> SEQUENCE: 5
gtcacacatg ctgcattgtg                                                 20

<210> SEQ ID NO 6
<211> LENGTH: 23
<212> TYPE: DNA
<213> ORGANISM: Artificial Sequence
<220> FEATURE:
<223> OTHER INFORMATION: B1c sequence

<400> SEQUENCE: 6
aacgcaacat aataaactct gca                                             23

<210> SEQ ID NO 7
<211> LENGTH: 22
<212> TYPE: DNA
<213> ORGANISM: Artificial
<220> FEATURE:
<223> OTHER INFORMATION: B2c sequence

<400> SEQUENCE: 7
ctgggctcat attgttattg at                                              22

<210> SEQ ID NO 8
<211> LENGTH: 22
<212> TYPE: DNA
<213> ORGANISM: Zaire ebolavirus

<400> SEQUENCE: 8
atcaataaca atatgagccc ag                                              22

<210> SEQ ID NO 9
<211> LENGTH: 22
<212> TYPE: DNA
<213> ORGANISM: Artificial Sequence
<220> FEATURE:
<223> OTHER INFORMATION: B3c sequence

<400> SEQUENCE: 9
tgttgtatca atatcttgcc ag                                              22

<210> SEQ ID NO 10
<211> LENGTH: 22
<212> TYPE: DNA
<213> ORGANISM: Zaire ebolavirus

<400> SEQUENCE: 10
ctggcaagat attgatacaa ca                                              22
```

-continued

```
<210> SEQ ID NO 11
<211> LENGTH: 19
<212> TYPE: DNA
<213> ORGANISM: Zaire ebolavirus

<400> SEQUENCE: 11
aattttttga ttatcacgc                                                    19

<210> SEQ ID NO 12
<211> LENGTH: 45
<212> TYPE: DNA
<213> ORGANISM: Artificial Sequence
<220> FEATURE:
<223> OTHER INFORMATION: sequence for FIT primer

<400> SEQUENCE: 12
gtcacacatg ctgcattgtg ttttctatat ttagcctctc tccct                       45

<210> SEQ ID NO 13
<211> LENGTH: 49
<212> TYPE: DNA
<213> ORGANISM: Artificial Sequence
<220> FEATURE:
<223> OTHER INFORMATION: sequence for BIT primer

<400> SEQUENCE: 13
aacgcaacat aataaactct gcattttatc aataacaata tgagcccag                   49

<210> SEQ ID NO 14
<211> LENGTH: 20
<212> TYPE: DNA
<213> ORGANISM: Artificial Sequence
<220> FEATURE:
<223> OTHER INFORMATION: F3 seqence

<400> SEQUENCE: 14
aataacgaaa ggagtcccta                                                   20

<210> SEQ ID NO 15
<211> LENGTH: 43
<212> TYPE: DNA
<213> ORGANISM: Artificial Sequence
<220> FEATURE:
<223> OTHER INFORMATION: sequence for BIT primer

<400> SEQUENCE: 15
gccgcaatga atttaacgca attttaatat gagcccagac ctt                         43

<210> SEQ ID NO 16
<211> LENGTH: 22
<212> TYPE: DNA
<213> ORGANISM: Zaire ebolavirus

<400> SEQUENCE: 16
ctgacaggat attgatacaa ca                                                22

<210> SEQ ID NO 17
<211> LENGTH: 20
<212> TYPE: DNA
<213> ORGANISM: Artificial Sequence
<220> FEATURE:
<223> OTHER INFORMATION: F3 sequence

<400> SEQUENCE: 17
ataacgaaag gagtccctat                                                   20
```

```
<210> SEQ ID NO 18
<211> LENGTH: 45
<212> TYPE: DNA
<213> ORGANISM: Artificial Sequence
<220> FEATURE:
<223> OTHER INFORMATION: sequence for FIP primer

<400> SEQUENCE: 18
tgtcacacat gctgcattgt tttttatatt tagcctctct ccctg            45

<210> SEQ ID NO 19
<211> LENGTH: 20
<212> TYPE: DNA
<213> ORGANISM: Zaire ebolavirus

<400> SEQUENCE: 19
cactattcca tctgacagga                                         20

<210> SEQ ID NO 20
<211> LENGTH: 20
<212> TYPE: DNA
<213> ORGANISM: Artificial Sequence
<220> FEATURE:
<223> OTHER INFORMATION: F3 sequence

<400> SEQUENCE: 20
gataacgaaa ggagtcctta                                         20

<210> SEQ ID NO 21
<211> LENGTH: 45
<212> TYPE: DNA
<213> ORGANISM: Artificial Sequence
<220> FEATURE:
<223> OTHER INFORMATION: sequence for FIP primer

<400> SEQUENCE: 21
gtcacacatg ctgtattgtg ttttctatat ttggcctctc tccct             45

<210> SEQ ID NO 22
<211> LENGTH: 19
<212> TYPE: DNA
<213> ORGANISM: Artificial Sequence
<220> FEATURE:
<223> OTHER INFORMATION: F3 sequence

<400> SEQUENCE: 22
tagataacga aaggagtcc                                          19

<210> SEQ ID NO 23
<211> LENGTH: 43
<212> TYPE: DNA
<213> ORGANISM: Artificial Sequence
<220> FEATURE:
<223> OTHER INFORMATION: sequence for BIP primer

<400> SEQUENCE: 23
gctgcaatga gtctaacgca attttaatat gagcccagac cta               43

<210> SEQ ID NO 24
<211> LENGTH: 43
<212> TYPE: DNA
<213> ORGANISM: Artificial Sequence
<220> FEATURE:
<223> OTHER INFORMATION: sequence for BIP primer
```

<400> SEQUENCE: 24
gctgcaatga gtctaacgca attttacaat atgagcccag acc    43

<210> SEQ ID NO 25
<211> LENGTH: 44
<212> TYPE: DNA
<213> ORGANISM: Artificial Sequence
<220> FEATURE:
<223> OTHER INFORMATION: sequence for BIP primer

<400> SEQUENCE: 25
ctgcaatgag tctaacgcaa cttttttatga gcccagacct ttcg    44

<210> SEQ ID NO 26
<211> LENGTH: 48
<212> TYPE: DNA
<213> ORGANISM: Artificial Sequence
<220> FEATURE:
<223> OTHER INFORMATION: sequence for BIP primer

<400> SEQUENCE: 26
gcaatgagtc taacgcaaca taataaactc atgagcccag acctttcg    48

<210> SEQ ID NO 27
<211> LENGTH: 48
<212> TYPE: DNA
<213> ORGANISM: Artificial Sequence
<220> FEATURE:
<223> OTHER INFORMATION: sequence for BIP primer

<400> SEQUENCE: 27
gcaatgagtc taacgcaaca taataaactc acaatatgag cccagacc    48

<210> SEQ ID NO 28
<211> LENGTH: 23
<212> TYPE: DNA
<213> ORGANISM: Artificial Sequence
<220> FEATURE:
<223> OTHER INFORMATION: sequence for LBc primer

<400> SEQUENCE: 28
ctctttataa ttaagcttta acg    23

<210> SEQ ID NO 29
<211> LENGTH: 38
<212> TYPE: DNA
<213> ORGANISM: Artificial Sequence
<220> FEATURE:
<223> OTHER INFORMATION: F3 sequence

<400> SEQUENCE: 29
caataaacaa ctatttaaat aacgaaagga gtccctat    38

<210> SEQ ID NO 30
<211> LENGTH: 22
<212> TYPE: DNA
<213> ORGANISM: Zaire ebolavirus

<400> SEQUENCE: 30
tgttgtatca atatcctgtc ag    22

<210> SEQ ID NO 31
<211> LENGTH: 25
<212> TYPE: DNA
<213> ORGANISM: Artificial Sequence

```
<220> FEATURE:
<223> OTHER INFORMATION: F1 sequence

<400> SEQUENCE: 31
cacaatgcag catgtgtgac atatt                                          25

<210> SEQ ID NO 32
<211> LENGTH: 29
<212> TYPE: DNA
<213> ORGANISM: Artificial Sequence
<220> FEATURE:
<223> OTHER INFORMATION: B1c sequence

<400> SEQUENCE: 32
gaatttaacg caacataata aactctgca                                      29

<210> SEQ ID NO 33
<211> LENGTH: 22
<212> TYPE: DNA
<213> ORGANISM: Artificial Sequence
<220> FEATURE:
<223> OTHER INFORMATION: B2c sequence

<400> SEQUENCE: 33
ctgggctcat attgttattg at                                             22

<210> SEQ ID NO 34
<211> LENGTH: 38
<212> TYPE: DNA
<213> ORGANISM: Artificial Sequence
<220> FEATURE:
<223> OTHER INFORMATION: B3c sequence

<400> SEQUENCE: 34
tgttgtatca atatcctgtc agatggaata gtgttttg                             38

<210> SEQ ID NO 35
<211> LENGTH: 38
<212> TYPE: DNA
<213> ORGANISM: Artificial Sequence
<220> FEATURE:
<223> OTHER INFORMATION: B3 sequence

<400> SEQUENCE: 35
caaaacacta ttccatctgg caagatattg atacaaca                             38

<210> SEQ ID NO 36
<211> LENGTH: 38
<212> TYPE: DNA
<213> ORGANISM: Artificial Sequence
<220> FEATURE:
<223> OTHER INFORMATION: F3 sequence

<400> SEQUENCE: 36
caataaacaa ctatttagat aacgaaagga gtccctat                             38

<210> SEQ ID NO 37
<211> LENGTH: 38
<212> TYPE: DNA
<213> ORGANISM: Zaire ebolavirus

<400> SEQUENCE: 37
caaaacacta ttccatctgg caggatattg atacaaca                             38
```

```
<210> SEQ ID NO 38
<211> LENGTH: 38
<212> TYPE: DNA
<213> ORGANISM: Artificial Sequence
<220> FEATURE:
<223> OTHER INFORMATION: F3 sequence

<400> SEQUENCE: 38
caataaataa ctatttaaat aacgaaagga gtccctat                              38

<210> SEQ ID NO 39
<211> LENGTH: 23
<212> TYPE: DNA
<213> ORGANISM: Artificial Sequence
<220> FEATURE:
<223> OTHER INFORMATION: F3 sequence

<400> SEQUENCE: 39
caataaataa ctatttaaat aac                                             23

<210> SEQ ID NO 40
<211> LENGTH: 22
<212> TYPE: DNA
<213> ORGANISM: Artificial Sequence
<220> FEATURE:
<223> OTHER INFORMATION: F3 sequence

<400> SEQUENCE: 40
ataactattt aaataacgaa ag                                              22

<210> SEQ ID NO 41
<211> LENGTH: 20
<212> TYPE: DNA
<213> ORGANISM: Artificial Sequence
<220> FEATURE:
<223> OTHER INFORMATION: F3 sequence

<400> SEQUENCE: 41
gataacgaaa ggagtcccta                                                 20

<210> SEQ ID NO 42
<211> LENGTH: 21
<212> TYPE: DNA
<213> ORGANISM: Artificial Sequence
<220> FEATURE:
<223> OTHER INFORMATION: F2 sequence

<400> SEQUENCE: 42
ctatatttgg cctctctccc t                                               21

<210> SEQ ID NO 43
<211> LENGTH: 21
<212> TYPE: DNA
<213> ORGANISM: Artificial Sequence
<220> FEATURE:
<223> OTHER INFORMATION: F2 sequence

<400> SEQUENCE: 43
tatatttagc ctctctccct g                                               21

<210> SEQ ID NO 44
<211> LENGTH: 20
<212> TYPE: DNA
<213> ORGANISM: Artificial Sequence
<220> FEATURE:
<223> OTHER INFORMATION: F1 sequence
```

```
<400> SEQUENCE: 44
cacaatacag catgtgtgac                                              20

<210> SEQ ID NO 45
<211> LENGTH: 19
<212> TYPE: DNA
<213> ORGANISM: Artificial Sequence
<220> FEATURE:
<223> OTHER INFORMATION: F1 sequence

<400> SEQUENCE: 45
acaatgcagc atgtgtgac                                               19

<210> SEQ ID NO 46
<211> LENGTH: 30
<212> TYPE: DNA
<213> ORGANISM: Artificial Sequence
<220> FEATURE:
<223> OTHER INFORMATION: B1c sequence

<400> SEQUENCE: 46
gcaatgagtc taacgcaaca taataaactc                                   30

<210> SEQ ID NO 47
<211> LENGTH: 21
<212> TYPE: DNA
<213> ORGANISM: Artificial Sequence
<220> FEATURE:
<223> OTHER INFORMATION: B1c sequence

<400> SEQUENCE: 47
ctgcaatgag tctaacgcaa c                                            21

<210> SEQ ID NO 48
<211> LENGTH: 21
<212> TYPE: DNA
<213> ORGANISM: Artificial Sequence
<220> FEATURE:
<223> OTHER INFORMATION: B1c sequence

<400> SEQUENCE: 48
gctgcaatga gtctaacgca a                                            21

<210> SEQ ID NO 49
<211> LENGTH: 21
<212> TYPE: DNA
<213> ORGANISM: Artificial Sequence
<220> FEATURE:
<223> OTHER INFORMATION: B1c sequence

<400> SEQUENCE: 49
gccgcaatga atttaacgca a                                            21

<210> SEQ ID NO 50
<211> LENGTH: 18
<212> TYPE: DNA
<213> ORGANISM: Artificial Sequence
<220> FEATURE:
<223> OTHER INFORMATION: B2c sequence

<400> SEQUENCE: 50
ggtctgggct catattgt                                                18
```

```
<210> SEQ ID NO 51
<211> LENGTH: 18
<212> TYPE: DNA
<213> ORGANISM: Artificial Sequence
<220> FEATURE:
<223> OTHER INFORMATION: B2c sequence

<400> SEQUENCE: 51
cgaaaggtct gggctcat                                                   18

<210> SEQ ID NO 52
<211> LENGTH: 19
<212> TYPE: DNA
<213> ORGANISM: Artificial Sequence
<220> FEATURE:
<223> OTHER INFORMATION: B2c sequence

<400> SEQUENCE: 52
cgaaaggtct gggctcata                                                  19

<210> SEQ ID NO 53
<211> LENGTH: 18
<212> TYPE: DNA
<213> ORGANISM: Artificial Sequence
<220> FEATURE:
<223> OTHER INFORMATION: B2c sequence

<400> SEQUENCE: 53
taggtctggg ctcatatt                                                   18

<210> SEQ ID NO 54
<211> LENGTH: 18
<212> TYPE: DNA
<213> ORGANISM: Artificial Sequence
<220> FEATURE:
<223> OTHER INFORMATION: B2c sequence

<400> SEQUENCE: 54
aaggtctggg ctcatatt                                                   18

<210> SEQ ID NO 55
<211> LENGTH: 38
<212> TYPE: DNA
<213> ORGANISM: Artificial Sequence
<220> FEATURE:
<223> OTHER INFORMATION: F3 sequence

<400> SEQUENCE: 55
caataaacaa ctatttaaat aacgaaagga gtccttat                             38

<210> SEQ ID NO 56
<211> LENGTH: 38
<212> TYPE: DNA
<213> ORGANISM: Artificial Sequence
<220> FEATURE:
<223> OTHER INFORMATION: F3 sequence

<400> SEQUENCE: 56
caataaataa ctatttaaat aacgaaagga gtccttat                             38

<210> SEQ ID NO 57
<211> LENGTH: 38
<212> TYPE: DNA
<213> ORGANISM: Artificial Sequence
<220> FEATURE:
<223> OTHER INFORMATION: F3 sequence
```

<400> SEQUENCE: 57
caataaataa ctatttagat aacgaaagga gtccctat                      38

<210> SEQ ID NO 58
<211> LENGTH: 38
<212> TYPE: DNA
<213> ORGANISM: Artificial Sequence
<220> FEATURE:
<223> OTHER INFORMATION: F3 sequence

<400> SEQUENCE: 58
caataaacaa ctatttagat aacgaaagga gtccttat                      38

<210> SEQ ID NO 59
<211> LENGTH: 38
<212> TYPE: DNA
<213> ORGANISM: Artificial Sequence
<220> FEATURE:
<223> OTHER INFORMATION: F3 sequence

<400> SEQUENCE: 59
caataaataa ctatttagat aacgaaagga gtccttat                      38

<210> SEQ ID NO 60
<211> LENGTH: 33
<212> TYPE: DNA
<213> ORGANISM: Artificial Sequence
<220> FEATURE:
<223> OTHER INFORMATION: F3 sequence

<400> SEQUENCE: 60
caataaataa ctatttaaat aacgaaagga gtc                           33

<210> SEQ ID NO 61
<211> LENGTH: 33
<212> TYPE: DNA
<213> ORGANISM: Artificial Sequence
<220> FEATURE:
<223> OTHER INFORMATION: F3 sequence

<400> SEQUENCE: 61
caataaataa ctatttagat aacgaaagga gtc                           33

<210> SEQ ID NO 62
<211> LENGTH: 22
<212> TYPE: DNA
<213> ORGANISM: Artificial Sequence
<220> FEATURE:
<223> OTHER INFORMATION: F2 sequence

<400> SEQUENCE: 62
ctatatttag cctctctccc tg                                       22

<210> SEQ ID NO 63
<211> LENGTH: 22
<212> TYPE: DNA
<213> ORGANISM: Artificial Sequence
<220> FEATURE:
<223> OTHER INFORMATION: F2 sequence

<400> SEQUENCE: 63
ctatatttgg cctctctccc tg                                       22

<210> SEQ ID NO 64
<211> LENGTH: 25
<212> TYPE: DNA
<213> ORGANISM: Artificial Sequence
<220> FEATURE:
<223> OTHER INFORMATION: F1 sequence

<400> SEQUENCE: 64
cacaatacag catgtgtgac atatt                                      25

<210> SEQ ID NO 65
<211> LENGTH: 30
<212> TYPE: DNA
<213> ORGANISM: Artificial Sequence
<220> FEATURE:
<223> OTHER INFORMATION: B2c sequence

<400> SEQUENCE: 65
cgataggtct gggctcatat tgttattgat                                 30

<210> SEQ ID NO 66
<211> LENGTH: 30
<212> TYPE: DNA
<213> ORGANISM: Artificial Sequence
<220> FEATURE:
<223> OTHER INFORMATION: B2c sequence

<400> SEQUENCE: 66
cgaaaggtct gggctcatat tgttattgat                                 30

<210> SEQ ID NO 67
<211> LENGTH: 38
<212> TYPE: DNA
<213> ORGANISM: Artificial Sequence
<220> FEATURE:
<223> OTHER INFORMATION: B3c sequence

<400> SEQUENCE: 67
tgttgtatca atatcttgtc agatggaata gtgttttg                        38

<210> SEQ ID NO 68
<211> LENGTH: 37
<212> TYPE: DNA
<213> ORGANISM: Artificial Sequence
<220> FEATURE:
<223> OTHER INFORMATION: B1c sequence

<400> SEQUENCE: 68
gccgcaatga atttaacgca acataataaa ctctgca                         37

<210> SEQ ID NO 69
<211> LENGTH: 37
<212> TYPE: DNA
<213> ORGANISM: Artificial Sequence
<220> FEATURE:
<223> OTHER INFORMATION: B1c sequence

<400> SEQUENCE: 69
gctgcaatga atttaacgca acataataaa ctctgca                         37

<210> SEQ ID NO 70
<211> LENGTH: 37
<212> TYPE: DNA
<213> ORGANISM: Artificial Sequence
<220> FEATURE:
<223> OTHER INFORMATION: B1c sequence

<400> SEQUENCE: 70
gccgcaatga gtttaacgca acataataaa ctctgca          37

<210> SEQ ID NO 71
<211> LENGTH: 37
<212> TYPE: DNA
<213> ORGANISM: Artificial Sequence
<220> FEATURE:
<223> OTHER INFORMATION: B1c sequence

<400> SEQUENCE: 71
gccgcaatga atctaacgca acataataaa ctctgca          37

<210> SEQ ID NO 72
<211> LENGTH: 37
<212> TYPE: DNA
<213> ORGANISM: Artificial Sequence
<220> FEATURE:
<223> OTHER INFORMATION: B1c sequence

<400> SEQUENCE: 72
gctgcaatga gtttaacgca acataataaa ctctgca          37

<210> SEQ ID NO 73
<211> LENGTH: 37
<212> TYPE: DNA
<213> ORGANISM: Artificial Sequence
<220> FEATURE:
<223> OTHER INFORMATION: B1c sequence

<400> SEQUENCE: 73
gccgcaatga gtctaacgca acataataaa ctctgca          37

<210> SEQ ID NO 74
<211> LENGTH: 36
<212> TYPE: DNA
<213> ORGANISM: Artificial Sequence
<220> FEATURE:
<223> OTHER INFORMATION: B1c sequence

<400> SEQUENCE: 74
ctgcaatgaa tctaacgcaa cataataaac tctgca          36

<210> SEQ ID NO 75
<211> LENGTH: 37
<212> TYPE: DNA
<213> ORGANISM: Artificial Sequence
<220> FEATURE:
<223> OTHER INFORMATION: B1c sequence

<400> SEQUENCE: 75
gctgcaatga gtctaacgca acataataaa ctctgca          37

<210> SEQ ID NO 76
<211> LENGTH: 18
<212> TYPE: DNA
<213> ORGANISM: Zaire ebolavirus

<400> SEQUENCE: 76
aattttttga ttatcacg          18

<210> SEQ ID NO 77
<211> LENGTH: 21
<212> TYPE: DNA
<213> ORGANISM: Artificial Sequence

```
<220> FEATURE:
<223> OTHER INFORMATION: LBc sequence

<400> SEQUENCE: 77
ctctttataa ttaagcttta a                                              21

<210> SEQ ID NO 78
<211> LENGTH: 21
<212> TYPE: DNA
<213> ORGANISM: Artificial Sequence
<220> FEATURE:
<223> OTHER INFORMATION: B2c sequence

<400> SEQUENCE: 78
ctgggctcat attgttattg a                                              21

<210> SEQ ID NO 79
<211> LENGTH: 20
<212> TYPE: DNA
<213> ORGANISM: Artificial Sequence
<220> FEATURE:
<223> OTHER INFORMATION: F1 sequence

<400> SEQUENCE: 79
cacaatacag catgtgtgac                                                20

<210> SEQ ID NO 80
<211> LENGTH: 21
<212> TYPE: DNA
<213> ORGANISM: Zaire ebolavirus

<400> SEQUENCE: 80
acactattcc atctgacagg a                                              21

<210> SEQ ID NO 81
<211> LENGTH: 20
<212> TYPE: DNA
<213> ORGANISM: Artificial Sequence
<220> FEATURE:
<223> OTHER INFORMATION: B3c sequence

<400> SEQUENCE: 81
tcctgtcaga tggaatagtg                                                20

<210> SEQ ID NO 82
<211> LENGTH: 38
<212> TYPE: DNA
<213> ORGANISM: Artificial Sequence
<220> FEATURE:
<223> OTHER INFORMATION: B3c sequence

<400> SEQUENCE: 82
tgttgtatca atatcttgcc agatggaata gtgttttg                             38

<210> SEQ ID NO 83
<211> LENGTH: 38
<212> TYPE: DNA
<213> ORGANISM: Artificial Sequence
<220> FEATURE:
<223> OTHER INFORMATION: B3c sequence

<400> SEQUENCE: 83
tgttgtatca atatcctgcc agatggaata gtgttttg                             38
```

```
<210> SEQ ID NO 84
<211> LENGTH: 20
<212> TYPE: DNA
<213> ORGANISM: Zaire ebolavirus

<400> SEQUENCE: 84
gtcacacatg ctgtattgtg                                               20

<210> SEQ ID NO 85
<211> LENGTH: 20
<212> TYPE: DNA
<213> ORGANISM: Zaire ebolavirus

<400> SEQUENCE: 85
tgtcacacat gctgcattgt                                               20

<210> SEQ ID NO 86
<211> LENGTH: 18
<212> TYPE: DNA
<213> ORGANISM: Zaire ebolavirus

<400> SEQUENCE: 86
acaatatgag cccagacc                                                 18

<210> SEQ ID NO 87
<211> LENGTH: 18
<212> TYPE: DNA
<213> ORGANISM: Zaire ebolavirus

<400> SEQUENCE: 87
atgagcccag acctttcg                                                 18

<210> SEQ ID NO 88
<211> LENGTH: 19
<212> TYPE: DNA
<213> ORGANISM: Zaire ebolavirus

<400> SEQUENCE: 88
tatgagccca gacctttcg                                                19

<210> SEQ ID NO 89
<211> LENGTH: 18
<212> TYPE: DNA
<213> ORGANISM: Zaire ebolavirus

<400> SEQUENCE: 89
aatatgagcc cagaccta                                                 18

<210> SEQ ID NO 90
<211> LENGTH: 18
<212> TYPE: DNA
<213> ORGANISM: Zaire ebolavirus

<400> SEQUENCE: 90
aatatgagcc cagacctt                                                 18

<210> SEQ ID NO 91
<211> LENGTH: 23
<212> TYPE: DNA
<213> ORGANISM: Zaire ebolavirus

<400> SEQUENCE: 91
tgcagagttt attatgttgc gtt                                           23
```

```
<210> SEQ ID NO 92
<211> LENGTH: 29
<212> TYPE: DNA
<213> ORGANISM: Zaire ebolavirus

<400> SEQUENCE: 92
tgcagtgttt attatgttgc gttaaattc                              29

<210> SEQ ID NO 93
<211> LENGTH: 30
<212> TYPE: DNA
<213> ORGANISM: Zaire ebolavirus

<400> SEQUENCE: 93
gagtttatta tgttgcgtta gactcattgc                             30

<210> SEQ ID NO 94
<211> LENGTH: 21
<212> TYPE: DNA
<213> ORGANISM: Zaire ebolavirus

<400> SEQUENCE: 94
gttgcgttag actcattgca g                                      21

<210> SEQ ID NO 95
<211> LENGTH: 21
<212> TYPE: DNA
<213> ORGANISM: Zaire ebolavirus

<400> SEQUENCE: 95
ttgcgttaga ctcattgcag c                                      21

<210> SEQ ID NO 96
<211> LENGTH: 21
<212> TYPE: DNA
<213> ORGANISM: Zaire ebolavirus

<400> SEQUENCE: 96
ttgcgttaaa ttcattgcgg c                                      21

<210> SEQ ID NO 97
<211> LENGTH: 37
<212> TYPE: DNA
<213> ORGANISM: Zaire ebolavirus

<400> SEQUENCE: 97
tgcagagttt attatgttgc gttaaattca ttgcggc                     37

<210> SEQ ID NO 98
<211> LENGTH: 37
<212> TYPE: DNA
<213> ORGANISM: Zaire ebolavirus

<400> SEQUENCE: 98
tgcagagttt attatgttgc gttaaattca ttgcagc                     37

<210> SEQ ID NO 99
<211> LENGTH: 37
<212> TYPE: DNA
<213> ORGANISM: Zaire ebolavirus

<400> SEQUENCE: 99
tgcagagttt attatgttgc gttaaactca ttgcggc                     37
```

```
<210> SEQ ID NO 100
<211> LENGTH: 37
<212> TYPE: DNA
<213> ORGANISM: Zaire ebolavirus

<400> SEQUENCE: 100
tgcagagttt attatgttgc gttagattca ttgcggc                             37

<210> SEQ ID NO 101
<211> LENGTH: 37
<212> TYPE: DNA
<213> ORGANISM: Zaire ebolavirus

<400> SEQUENCE: 101
tgcagagttt attatgttgc gttaaactca ttgcagc                             37

<210> SEQ ID NO 102
<211> LENGTH: 37
<212> TYPE: DNA
<213> ORGANISM: Zaire ebolavirus

<400> SEQUENCE: 102
tgcagagttt attatgttgc gttagactca ttgcggc                             37

<210> SEQ ID NO 103
<211> LENGTH: 36
<212> TYPE: DNA
<213> ORGANISM: Zaire ebolavirus

<400> SEQUENCE: 103
tgcagagttt attatgttgc gttagattca ttgcag                              36

<210> SEQ ID NO 104
<211> LENGTH: 37
<212> TYPE: DNA
<213> ORGANISM: Zaire ebolavirus

<400> SEQUENCE: 104
tgcagagttt attatgttgc gttagactca ttgcagc                             37
```

PRIMER SET FOR DETECTION OF ZAIRE EBOLA VIRUS, ASSAY KIT, AND AMPLIFICATION METHOD

CROSS-REFERENCE TO RELATED APPLICATIONS

This application is a Continuation Application of PCT Application No. PCT/JP2015/085534, filed Dec. 18, 2015 and based upon and claiming the benefit of priority from Japanese Patent Application No. 2014-258074, filed Dec. 19, 2014; and No. 2015-123538, filed Jun. 19, 2015, the entire contents of all of which are incorporated herein by reference.

FIELD

Embodiments described herein relate generally to a primer set for detection of Zaire ebolavirus, an assay kit, and an amplification method.

BACKGROUND

Ebola virus (EBOV) is a virus with which humans and primates other than humans are infected and which is deadly to them with high probability.

There are five species of EBOV including Zaire ebolavirus (ZEBOV), Sudan ebolavirus (SEBOV), Taï forest ebolavirus (the former Ivory Coast ebolavirus) (ICEBOV), Bundibugyo ebolavirus (BEBOV), and Reston ebolavirus (REBOV). Among them, the ZEBOV, SEBOV, ICEBOV, and BEBOV are known to be pathogenic to the humans.

Among the species, the fatality rate from the ZEBOV is 90% and it is known to be as the virus with the highest pathogenicity.

The ZEBOV is detected by a pathological method, a method based on an antigen-antibody reaction using a monoclonal antibody, a PCR method using a specific primer set or the like.

As of 2014, in view of the epidemic spread of Ebola virus, there is a need for development of a unit capable of detecting ZEBOV with high accuracy.

BRIEF DESCRIPTION OF THE DRAWINGS

FIG. 1B is a pattern diagram showing matching of each template nucleic acid to each primer.

FIG. 2C is a view showing an example of cDNA of Zaire Ebola virus genome and each primer recognition region corresponding to the cDNA.

FIG. 3B is a view showing an example of cDNA of Zaire Ebola virus genome and each primer recognition region corresponding to the cDNA.

FIG. 5A is a graph showing the experimental results.
FIG. 5B is a graph showing the experimental results.
FIG. 5C is a graph showing the experimental results.
FIG. 5D is a graph showing the experimental results.
FIG. 5E is a graph showing the experimental results.
FIG. 5F is a graph showing the experimental results.
FIG. 5K is a graph showing the experimental results.
FIG. 5L is a graph showing the experimental results.

DETAILED DESCRIPTION

ZEBOV is a non-segmented negative strand RNA virus and has a length of about 19 kb. A leader region and a trailer region which are non-coding sequences are present at the 3' end and the 5' end of the gene of the virus, respectively.

The embodiments are based on the discovery in which a primer region is designed using a specific sequence of the trailer region, thereby achieving detection of the ZEBOV strain which could not be detected before.

According to the primer set of each of the embodiments, it is possible to detect a ZEBOV strain isolated in Guinea, 2014 (Guinea 14 strain). In order to reduce the epidemic spread of the ZEBOV in 2014, it is essential to detect the ZEBOV accurately and rapidly. To achieve this, it is essential to detect the Guinea 14 strain. The conventional primer set cannot detect the Guinea 14 strain, but, according to the primer set of each of the embodiments, it is possible to detect not only a 1976 Zaire strain which ran rampant in the past strain isolated in Zaire, 1976 (Zaire 76 strain) and a strain isolated in Zaire, 1995 (Zaire 95 strain), but also the Guinea 14 strain. This enables the ZEBOV to be detected with high accuracy.

The primer region according to each of the embodiments will be described with reference to FIGS. 1A and 1B.

Figure 1A:
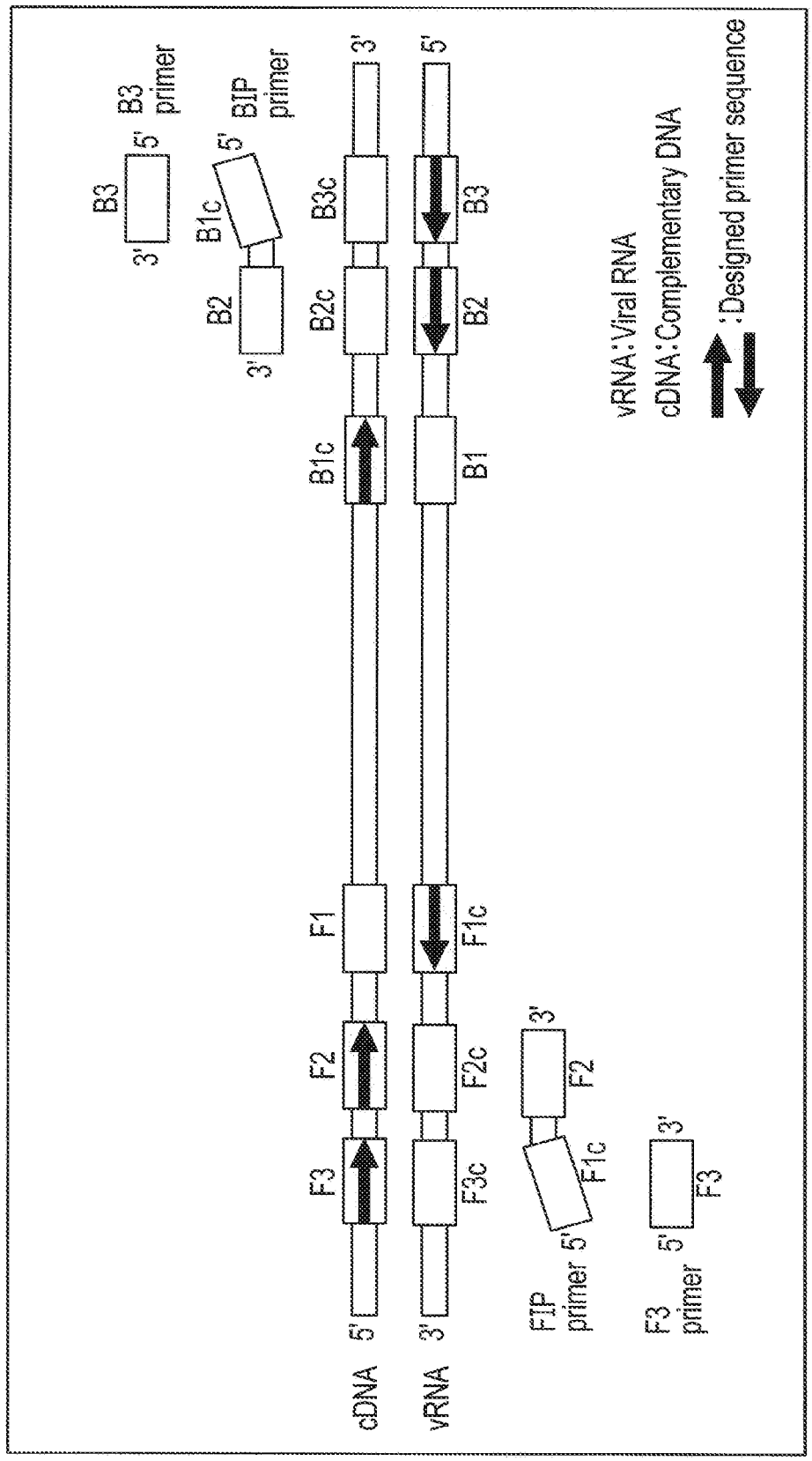
FIG. 1A is a pattern diagram showing matching of each template nucleic acid to each primer.

FIG. 1A is a view showing a ZEBOV RNA as a template (shown as "vRNA" in the figure), a complementary DNA (cDNA) of the ZEBOV RNA, and primers matched to the RNA and the cDNA. The ZEBOV RNA to be detected includes an F3c region, an F2c region, an F1c region, a B1 region, a B2 region, and a B3 region as regions to which each of the primers is bound (i.e., recognition regions). These regions are included in the ZEBOV RNA from the 3' side towards the 5' side in this order. Each of these regions includes an F3c sequence, an F2c sequence, an F1c sequence, a B1 sequence, a B2 sequence, and a B3 sequence. These sequences and complementary sequences to them i.e., the F3 sequence, the F2 sequence, the F1 sequence, the B1c sequence, the B2c sequence, and the B3c sequence are referred to as "recognition sequences". The ZEBOV RNA is used as a first template sequence.

cDNA is a complementary strand of the ZEBOV RNA and includes an F3 sequence, an F2 sequence, an F1 sequence, a B1c sequence, a B2c sequence, and a B3c sequence from the 5' side toward the 3' side. The cDNA is made from the ZEBOV RNA contained in a sample to be subjected to a test by a reverse transcription reaction, and an amplification reaction of template nucleic acids of the cDNA and the ZEBOV RNA is performed using the primer set of each of the embodiments.

Here, F1 and F1c sequences are complementary to each other, F2 and F2c sequences are complementary to each other, F3 and F3c sequences are complementary to each other, B1 and B1c sequences are complementary to each other, B2 and B2c sequences are complementary to each other, and B3 and B3c sequences are complementary to each other.

As for such template sequences, a primer set including internal primers (FIP and BIP primers) and two external primers (F3 and B3 primers), which correspond to the above six recognition regions, is designed as a set.

The primer set according to each of the embodiments includes an FIP primer, an F3 primer, a BIP primer, and a B3 primer. The FIP primer includes an F1c sequence and a F2 sequence from the 5' side toward the 3' side. The F3 primer includes an F3 sequence. The BIP primer includes a B1c sequence and a B2 sequence from the 5' side toward the 3' side. The B3 primer includes a B3 sequence. The regions corresponding to the sequences of these primers are indicated by arrows in FIG. 1A. The direction of each arrow indicates the directionality of each primer sequence corresponding to each region, and a start point and an end point of an arrow indicate the 5' end and the 3' end, respectively.

The primer set according to one of the embodiments may further include an LF primer and/or LB primer as a loop primer. FIG. 1B shows an example of the designed sequences of the LF primer and the LB primer, in addition to the designed primer sequences of FIG. 1A.

The ZEBOV RNA includes an F3c region, an F2c region, an LFc region, an F1c region, a B1 region, an LB region, a B2 region, and a B3 region as primer recognition regions. These regions are included in the ZEBOV RNA from the 3' side towards the 5' side in this order. The LFc region and the LB region include an LFc sequence and an LB sequence, respectively. The ZEBOV RNA is used as a template sequence.

Alternatively, the loop primer may be designed to be bound to, for example, a loop portion of an amplified product. The loop portion may be a region shown as a single-stranded portion in FIG. 1B. That is, the loop region may be, for example, a region from the 5' end of the F2c region of vRNA to the base closer to the 3' side than the 3' end of the F1c region or may be a region from the 3' end of the B2 region of vRNA to the base closer to the 5' side than the 5' end of the B1 region.

The sequences of respective primers are determined by comparing to sequences of 130 strains according to Accession numbers shown in Table 1.

TABLE 1

| Accession No. (Genbank) | | | | | |
|---|---|---|---|---|---|
| NC_002549 | KM034551 | KM034558 | KM233117 | KM233116 | KM233115 |
| KJ660346 | KM233114 | KM233113 | KJ660347 | KM233112 | KJ660348 |
| KM034549 | KM233111 | KM233110 | KM233109 | KM034550 | K4034552 |
| KM233108 | KM034553 | KM034554 | KM034555 | KM034556 | KM034557 |
| KM233107 | KM233106 | KM034559 | KM233105 | KM233104 | KM233103 |
| KM034560 | KM233102 | KM233101 | KM034561 | KM034562 | KM034563 |
| KM233100 | KM233099 | KM233098 | KM233097 | KM233035 | KM233036 |
| KM233096 | KM233037 | KM233095 | KM233094 | KM233038 | KM233093 |
| KM233039 | KM233040 | KM233092 | KM233091 | KM233090 | KM233089 |
| KM233088 | KM233087 | KM233086 | KM233085 | KM233084 | K4233083 |
| KM233082 | KM233081 | KM233080 | KM233079 | KM233078 | KM233077 |
| KM233076 | KM233075 | KM233074 | KM233073 | KM233072 | KM233071 |
| KM233041 | KM233042 | KM233043 | KM233044 | KM233045 | KM233046 |
| KM233047 | KM233048 | KM233049 | KM233050 | KM233051 | KM233052 |
| KM233053 | KM233054 | KM233055 | KM233070 | KM233069 | KM233068 |
| KM233067 | KM233066 | KM233065 | KM233064 | KM233063 | KM233062 |
| KM233061 | KM233060 | KM233059 | KM233056 | KM233057 | KM233058 |
| KM233118 | KF827427 | AF086833 | AF272001 | AF499101 | AY142960 |
| EU224440 | KC242791 | KC242801 | KC242796 | KC242799 | AY354458 |
| KC242793 | KC242795 | KC242797 | KC242792 | KC242794 | KC242798 |
| KC242789 | KC242790 | KC242788 | KC242787 | KC242785 | KC242784 |
| HQ613403 | HQ613402 | KC242786 | KC242800 | | |

The names of the strains are shown in Table 2.

TABLE 2

| Accession No. | Strain's name |
|---|---|
| NC_002549 | EBOV/*H. sapiens*-tc/COD/1976/Yambuku-Mayinga |
| KM034551 | EBOV/*H. sapiens*-wt/SLE/2014/Makona-EM096 |
| KM034558 | EBOV/*H. sapiens*-wt/SLE/2014/Makona-G3679.1 |
| KM233117 | EBOV/*H. sapiens*-wt/SLE/2014/Makona-NM042.2 |
| KM233116 | EBOV/*H. sapiens*-wt/SLE/2014/Makona-NM042.1 |
| KM233115 | EBOV/*H. sapiens*-wt/SLE/2014/Makona-G3857 |
| KJ660346 | EBOV/*H. sapiens*-wt/GIN/2014/Kissidougou-C15 |
| KM233114 | EBOV/*H. sapiens*-wt/SLE/2014/Makona-G3856.3 |
| KM233113 | EBOV/*H. sapiens*-wt/SLE/2014/Makona-G3856.1 |
| KJ660347 | EBOV/*H. sapiens*-wt/GIN/2014/Gueckedou-C07 |
| KM233112 | EBOV/*H. sapiens*-wt/SLE/2014/Makona-G3851 |
| KJ660348 | EBOV/*H. sapiens*-wt/GIN/2014/Gueckedou-C05 |
| KM034549 | EBOV/*H. sapiens*-wt/SLE/2014/Makona-EM095B |
| KM233111 | EBOV/*H. sapiens*-wt/SLE/2014/Makona-G3850 |
| KM233110 | EBOV/*H. sapiens*-wt/SLE/2014/Makona-G3848 |
| KM233109 | EBOV/*H. sapiens*-wt/SLE/2014/Makona-G3846 |
| KM034550 | EBOV/*H. sapiens*-wt/SLE/2014/Makona-EM095 |
| KM034552 | EBOV/*H. sapiens*-wt/SLE/2014/Makona-EM098 |
| KM233108 | EBOV/*H. sapiens*-wt/SLE/2014/Makona-G3845 |
| KM034553 | EBOV/*H. sapiens*-wt/SLE/2014/Makona-G3670.1 |
| KM034554 | EBOV/*H. sapiens*-wt/SLE/2014/Makona-G3676.1 |
| KM034555 | EBOV/*H. sapiens*-wt/SLE/2014/Makona-G3676.2 |
| KM034556 | EBOV/*H. sapiens*-wt/SLE/2014/Makona-G3677.1 |
| KM034557 | EBOV/*H. sapiens*-wt/SLE/2014/Makona-G3677.2 |
| KM233107 | EBOV/*H. sapiens*-wt/SLE/2014/Makona-G3841 |
| KM233106 | EBOV/*H. sapiens*-wt/SLE/2014/Makona-G3840 |
| KM034559 | EBOV/*H. sapiens*-wt/SLE/2014/Makona-G3680.1 |
| KM233105 | EBOV/*H. sapiens*-wt/SLE/2014/Makona-G3838 |
| KM233104 | EBOV/*H. sapiens*-wt/SLE/2014/Makona-G3834 |
| KM233103 | EBOV/*H. sapiens*-wt/SLE/2014/Makona-G3831 |
| KM034560 | EBOV/*H. sapiens*-wt/SLE/2014/Makona-G3682.1 |
| KM233102 | EBOV/*H. sapiens*-wt/SLE/2014/Makona-G3829 |
| KM233101 | EBOV/*H. sapiens*-wt/SLE/2014/Makona-G3827 |
| KM034561 | EBOV/*H. sapiens*-wt/SLE/2014/Makona-G3683.1 |
| KM034562 | EBOV/*H. sapiens*-wt/SLE/2014/Makona-G3686.1 |
| KM034563 | EBOV/*H. sapiens*-wt/SLE/2014/Makona-G3687.1 |
| KM233100 | EBOV/*H. sapiens*-wt/SLE/2014/Makona-G3826 |
| KM233099 | EBOV/*H. sapiens*-wt/SLE/2014/Makona-G3825.2 |
| KM233098 | EBOV/*H. sapiens*-wt/SLE/2014/Makona-G3825.1 |
| KM233097 | EBOV/*H. sapiens*-wt/SLE/2014/Makona-G3823 |
| KM233035 | EBOV/*H. sapiens*-wt/SLE/2014/Makona-EM104 |
| KM233036 | EBOV/*H. sapiens*-wt/SLE/2014/Makona-EM106 |
| KM233096 | EBOV/*H. sapiens*-wt/SLE/2014/Makona-G3822 |
| KM233037 | EBOV/*H. sapiens*-wt/SLE/2014/Makona-EM110 |

TABLE 2-continued

| Accession No. | Strain's name |
|---|---|
| KM233095 | EBOV/*H. sapiens*-wt/SLE/2014/Makona-G3821 |
| KM233094 | EBOV/*H. sapiens*-wt/SLE/2014/Makona-G3820 |
| KM233038 | EBOV/*H. sapiens*-wt/SLE/2014/Makona-EM111 |
| KM233093 | EBOV/*H. sapiens*-wt/SLE/2014/Makona-G3819 |
| KM233039 | EBOV/*H. sapiens*-wt/SLE/2014/Makona-EM112 |
| KM233040 | EBOV/*H. sapiens*-wt/SLE/2014/Makona-EM113 |
| KM233092 | EBOV/*H. sapiens*-wt/SLE/2011/Makona-G3818 |
| KM233091 | EBOV/*H. sapiens*-wt/SLE/2014/Makona-G3817 |
| KM233090 | EBOV/*H. sapiens*-wt/SLE/2014/Makona-G3816 |
| KM233089 | EBOV/*H. sapiens*-wt/SLE/2014/Makona-G3814 |
| KM233088 | EBOV/*H. sapiens*-wt/SLE/2014/Makona-G3810.2 |
| KM233087 | EBOV/*H. sapiens*-wt/SLE/2014/Makona-G3810.1 |
| KM233086 | EBOV/*H. sapiens*-wt/SLE/2014/Makona-G3809 |
| KM233085 | EBOV/*H. sapiens*-wt/SLE/2014/Makona-G3808 |
| KM233084 | EBOV/*H. sapiens*-wt/SLE/2014/Makona-G3805.2 |
| KM233083 | EBOV/*H. sapiens*-wt/SLE/2014/Makona-G3805.1 |
| KM233082 | EBOV/*H. sapiens*-wt/SLE/2014/Makona-G3800 |
| KM233081 | EBOV/*H. sapiens*-wt/SLE/2014/Makona-G3799 |
| KM233080 | EBOV/*H. sapiens*-wt/SLE/2014/Makona-G3798 |
| KM233079 | EBOV/*H. sapiens*-wt/SLE/2014/Makona-G3796 |
| KM233078 | EBOV/*H. sapiens*-wt/SLE/2014/Makona-G3795 |
| KM233077 | EBOV/*H. sapiens*-wt/SLE/2014/Makona-G3789.1 |
| KM233076 | EBOV/*H. sapiens*-wt/SLE/2014/Makona-G3788 |
| KM233075 | EBOV/*H. sapiens*-wt/SLE/2014/Makona-G3787 |
| KM233071 | EBOV/*H. sapiens*-wt/SLE/2014/Makona-G3786 |
| KM233073 | EBOV/*H. sapiens*-wt/SLE/2014/Makona-G3782 |
| KM233072 | EBOV/*H. sapiens*-wt/SLE/2014/Makona-G3771 |
| KM233071 | EBOV/*H. sapiens*-wt/SLE/2014/Makona-EM115 |
| KM233041 | EBOV/*H. sapiens*-wt/SLE/2014/Makona-EM119 |
| KM233042 | EBOV/*H. sapiens*-wt/SLE/2014/Makona-EM120 |
| KM233043 | EBOV/*H. sapiens*-wt/SLE/2014/Makona-EM121 |
| KM233044 | EBOV/*H. sapiens*-wt/SLE/2014/Makona-EM124.1 |
| KM233045 | EBOV/*H. sapiens*-wt/SLE/2014/Makona-EM124.2 |
| KM233046 | EBOV/*H. sapiens*-wt/SLE/2014/Makona-EM124.3 |
| KM233047 | EBOV/*H. sapiens*-wt/SLE/2014/Makona-EM124.4 |
| KM233048 | EBOV/*H. sapiens*-wt/SLE/2014/Makona-G3707 |
| KM233049 | EBOV/*H. sapiens*-wt/SLE/2014/Makona-G3713.2 |
| KM233050 | EBOV/*H. sapiens*-wt/SLE/2014/Makona-G3713.3 |
| KM233051 | EBOV/*H. sapiens*-wt/SLE/2014/Makona-G3713.4 |
| KM233052 | EBOV/*H. sapiens*-wt/SLE/2014/Makona-G3724 |
| KM233053 | EBOV/*H. sapiens*-wt/SLE/2014/Makona-G3729 |
| KM233054 | EBOV/*H. sapiens*-wt/SLE/2014/Makona-G3734.1 |
| KM233055 | EBOV/*H. sapiens*-wt/SLE/2014/Makona-G3805.2 |
| KM233070 | EBOV/*H. sapiens*-wt/SLE/2014/Makona-G3770.2 |
| KM233069 | EBOV/*H. sapiens*-wt/SLE/2014/Makona-G3770.1 |
| KM233068 | EBOV/*H. sapiens*-wt/SLE/2014/Makona-G3769.4 |
| KM233067 | EBOV/*H. sapiens*-wt/SLE/2014/Makona-G3769.3 |
| KM233066 | EBOV/*H. sapiens*-wt/SLE/2014/Makona-G3769.2 |
| KM233065 | EBOV/*H. sapiens*-wt/SLE/2014/Makona-G3769.1 |
| KM233064 | EBOV/*H. sapiens*-wt/SLE/2014/Makona-G3765.2 |
| KM233063 | EBOV/*H. sapiens*-wt/SLE/2014/Makona-G3764 |
| KM233062 | EBOV/*H. sapiens*-wt/SLE/2014/Makona-G3758 |
| KM233061 | EBOV/*H. sapiens*-wt/SLE/2014/Makona-G3752 |
| KM233060 | EBOV/*H. sapiens*-wt/SLE/2014/Makona-G3750.3 |
| KM233059 | EBOV/*H. sapiens*-wt/SLE/2014/Makona-G3750.2 |
| KM233056 | EBOV/*H. sapiens*-wt/SLE/2014/Makona-G3735.1 |
| KM233057 | EBOV/*H. sapiens*-wt/SLE/2014/Makona-G3735.2 |
| KM233058 | EBOV/*H. sapiens*-wt/SLE/2014/Makona-G3750.1 |
| KM233118 | EBOV/*H. sapiens*-wt/SLE/2014/Makona-NM042.3 |
| KF827427 | Mutant Myainga76 |
| AF086833 | Mayinga76 |
| AF272001 | Mayinga76 |
| AF499101 | Mayinga76 |
| AY142960 | Mayinga76 |
| EU224440 | Mayinga76 |
| KC242791 | EBOV/*H. sapiens*-tc/COD/1977/Bonduni |
| KC242801 | EBOV/*H. sapiens*-tc/COD/1976/deRoover |
| KC242796 | EBOV/*H. sapiens*-tc/COD/1995/13625 Kikwit |
| KC242799 | EBOV/*H. sapiens*-tc/COD/1995/13709 Kikwit |
| AY354458 | Zaire 1995 |
| KC242793 | EBOV/*H. sapiens*-tc/GAB/1996/1Eko |
| KC242795 | EBOV/*H. sapiens*-tc/GAB/1996/1Mbie |
| KC242797 | EBOV/*H. sapiens*-tc/GAB/1996/1Oba |
| KC242792 | EBOV/*H. sapiens*-tc/GAB/1994/Gabon |
| KC242794 | EBOV/*H. sapiens*-tc/GAB/1996/2Nza |
| KC242798 | EBOV/*H. sapiens*-tc/GAB/1996/1Ikot |
| KC242789 | EBOV/*H. sapiens*-tc/COD/2007/4 Luebo |

TABLE 2-continued

| Accession No. | Strain's name |
|---|---|
| KC242790 | EBOV/*H. sapiens*-tc/COD/2007/5 Luebo |
| KC242788 | EBOV/*H. sapiens*-tc/COD/2007/43 Luebo |
| KC242787 | EBOV/*H. sapiens*-tc/COD/2007/23 Luebo |
| KC242785 | EBOV/*H. sapiens*-tc/COD/2007/0 Luebo |
| KC242784 | EBOV/*H. sapiens*-tc/COD/2007/9 Luebo |
| HQ613403 | EBOV/*H. sapiens*-tc/COD/2007/M-M |
| HQ613402 | EBOV/*H. sapiens*-tc/COD/2008/034-KS |
| KC242786 | EBOV/*H. sapiens*-tc/COD/2007/1 Luebo |
| KC242800 | EBOV/*H. sapiens*-tc/GAB/1996/Ilembe |

Comparison of the above 130 strains was performed by creating alignments. The used region includes sequences 18299-18658 in the cDNA region corresponding to the trailer sequences of the each strains.

In the design of the primer recognition region, an LAMP primer design support software program (PrimerExplorer ver.3; Net Laboratory, Tokyo (Japan); http://primerexplorer.jp/e/) was used to design a basic region. Then, while taking into consideration information from alignment and experimental results, the position on cDNA and the type of base were changed and adjusted manually and visually.

The designed basic region is a Tr2-based region. Tr2-based F3, F2, F1, B1c, B2c, and B3c regions are regions at positions 18339-18358, at positions 18368-18388, at positions 18408-18427, at positions 18449-18471, at positions 18501-18522, and at positions 18543-18562, respectively.

Further, T273-based regions and 5'UTR-based regions are designed by modifying and adjusting the Tr2-based regions.

T237-based F3, F2, F1, B1c, B2c, and B3c regions are regions at positions 18338-18357, at positions 18367-18387, at positions 18407-18426, at positions 18435-18455, at positions 18496-18513, and at positions 18530-18551, respectively.

5'UTR-based F3, F2, F1, B1c, B2c, and B3c regions are regions at positions 18321-18343, at positions 18367-18387, at positions 18407-18426, at positions 18449-18471, and at positions 18501-18522, and at positions 18530-18551, respectively. Further, the region at positions 18388-18406 is an LF region.

Figure 2A:
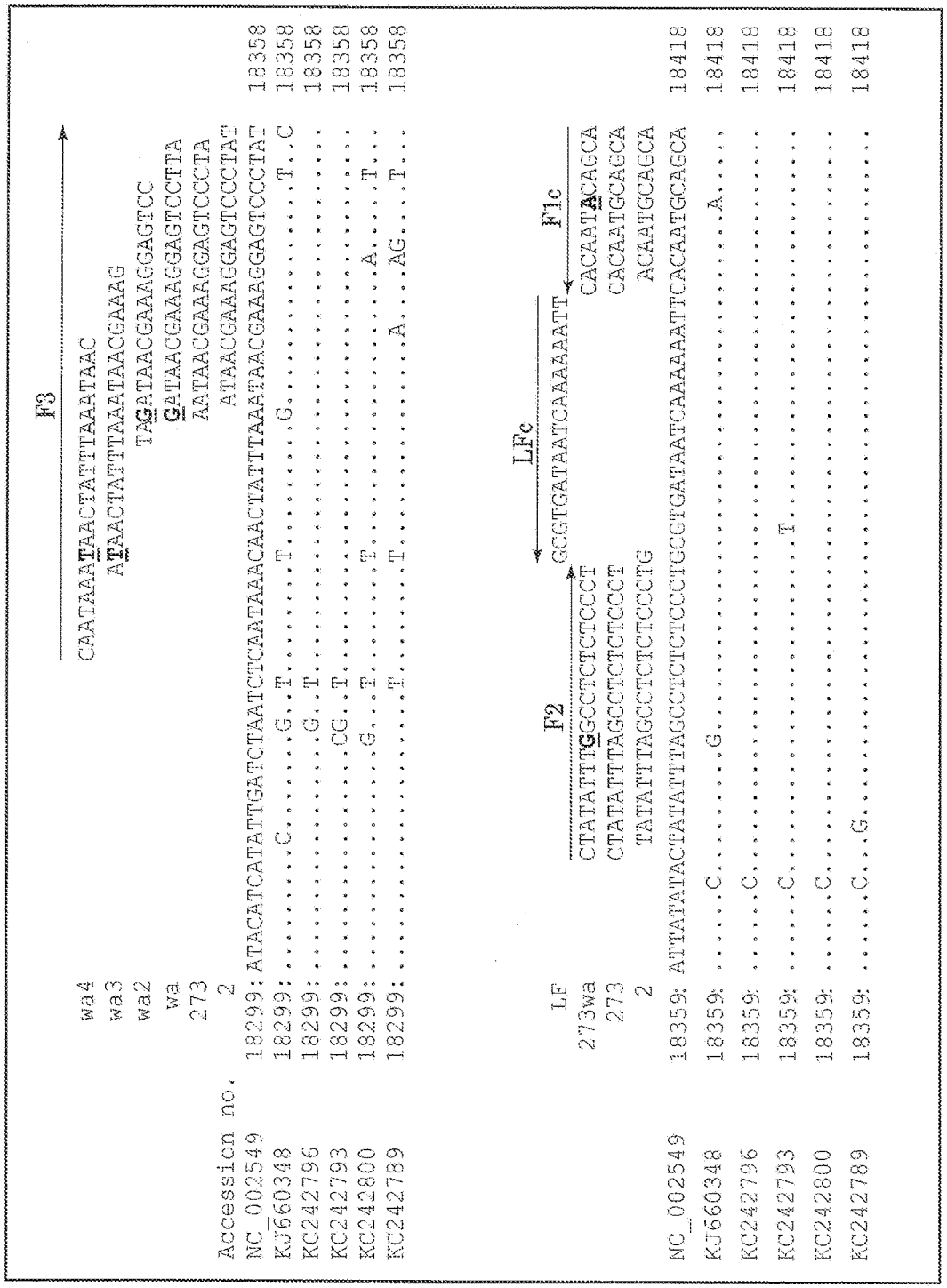
FIG. 2A is a view showing an example of cDNA of Zaire Ebola virus genome and each primer recognition region corresponding to the cDNA.
Figure 2B:
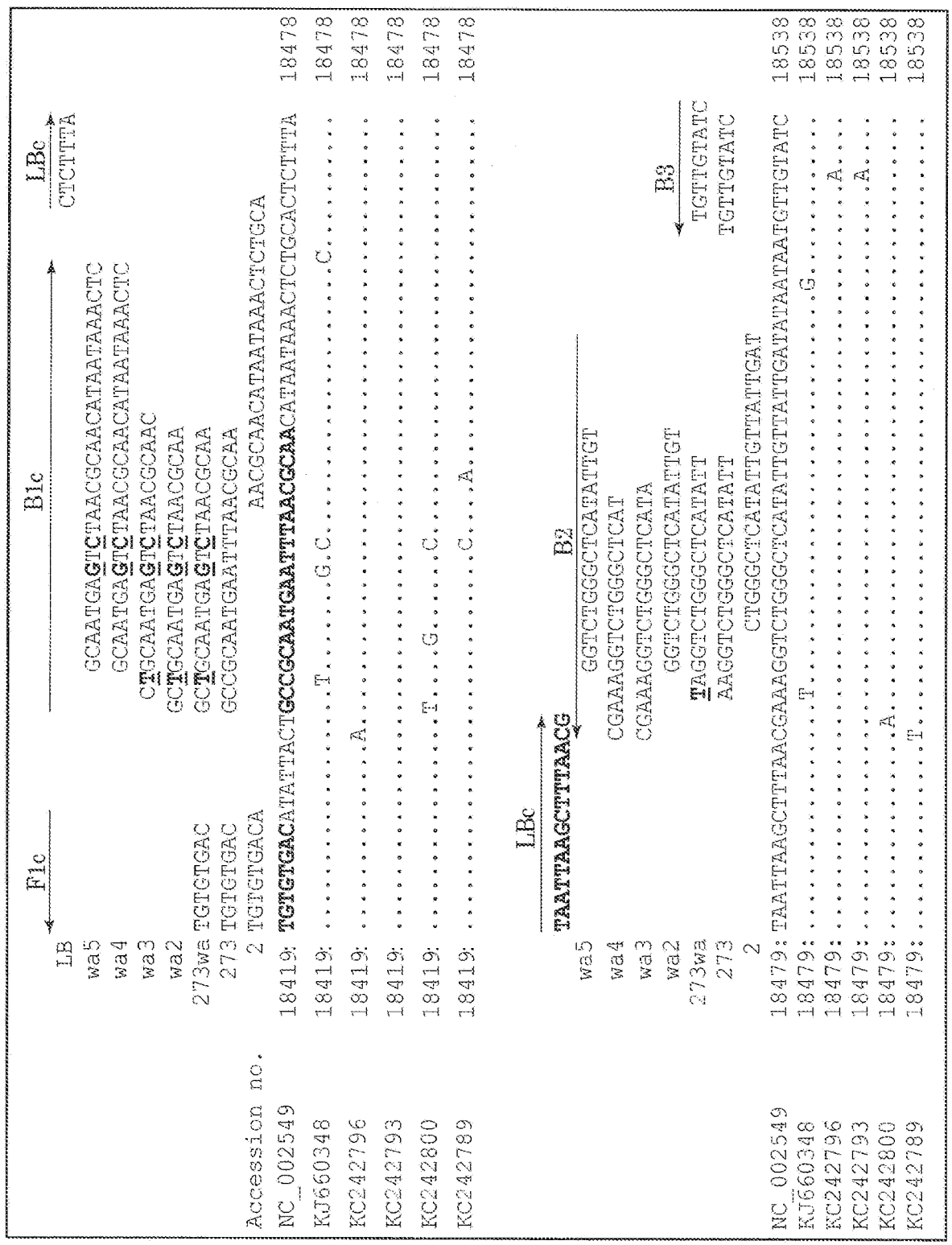
FIG. 2B is a view showing an example of cDNA of Zaire Ebola virus genome and each primer recognition region corresponding to the cDNA.
Figure 2C:
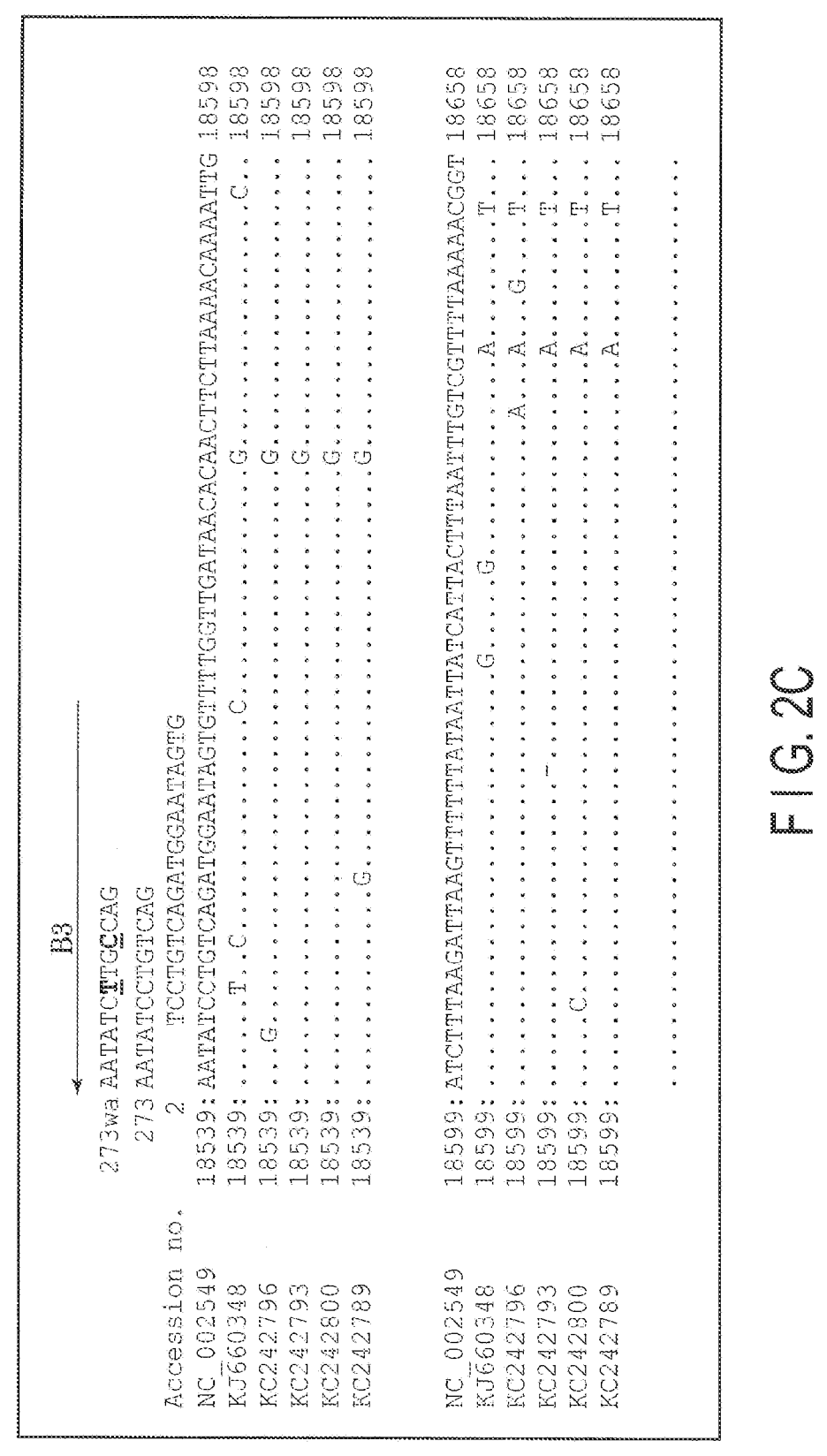

FIGS. 2A to 2C show the alignment of cDNA of the Zaire 76 strain (*H. sapiens*-tc/COD/1976/Yambuku-Mayinga) as a consensus sequence in the 5' to 3' direction with cDNAs of Guinea 14 strain (*H. sapiens*-wt/GIN/2014-/Gueckedou-C05), Zaire 95 strain (EBOV/*H. sapiens*-tc/COD/1995/13625 Kikwit), two types of Gabon 96 strains (EBOV/*H. sapiens*-tc/GAB/1996/1Eko, EBOV/*H. sapiens*-tc/GAB/1996/Ilembe), and Zaire 07 strain (EBOV/*H. sapiens*-tc/COD/2007/4 Luebo) and examples of the design of the primer recognition sequence. The sequences shown therein represent 360 bases at sequences 18299-18658 in the cDNA region corresponding to the trailer sequence of the Zaire Ebola virus in the 5' to 3' direction.

Further, FIGS. 2A to 2C show Tr2-based, Tr273-based, and 5'UTR-based, (i.e., Tr273wa-based, Tr273wa2-based, Tr273wa3-based, Tr273wa4-based, and Tr273wa5-based) primer recognition sequences to be matched to the primer recognition region of cDNA.

The primers designed from these sequences are shown in Table 3. This table shows the primer sequences, corresponding SEQ ID numbers, and the correspondences of the sequences shown in FIGS. 2A to 2C.

TABLE 3

| Primer's name | Sequence | SEQ ID No. | Matching of FIG. 2 (SEQ ID No.) (c: complimentary sequence) | |
|---|---|---|---|---|
| Tr273_F3 | 5' AATAACGAAAG GAGTCCCTA 3' | 14 | 14 | |
| Tr273_FIP | 5' GTCACACATGC TGCATTGTGttttC TATATTTAGCCTCT CTCCCT 3' | 12 | F1c 5 | F2 3 |
| Tr273_BIP | 5' GCCGCAATGAA TTTAACGCAAtttt AATATGAGCCCAGA CCTT 3' | 15 | B1c 49 | B2 54c(90) |
| Tr273_B3 | 5' CTGACAGGATA TTGATACAACA 3' | 16 | 16 | |
| Tr273_LB | 5' CTCTTTATAAT TAAGCTTTAACG 3' | 28 | 28 | |
| Tr2_F3 | 5' ATAACGAAAGG AGTCCCTAT 3' | 17 | 17 | |
| Tr2_FIP | 5' TGTCACACATG CTGCATTGTttttT ATATTTAGCCTCTC TCCCTG 3' | 18 | F1c 45c(85) | F2 43 |
| Tr2_BIP | 5' AACGCAACATA ATAAACTCTGCAtt ttATCAATAACAAT ATGAGCCCAG 3' | 13 | B1c 6 | B2 8(7c) |
| Tr2_B3 | 5' CACTATTCCAT CTGACAGGA 3' | 19 | 19 | |
| Tr2_LF | 5' AATTTTTTGAT TATCACG 3' | 76 | 76 | |
| Tr2_LB | 5' CTCTTTATAAT TAAGCTTTAACG 3' | 28 | 28 | |
| Tr273wa_F3 | 5' GATAACGAAAG GAGTCCTTA 3' | 20 | 20 | |
| Tr273wa2_F3 | 5' TAGATAACGAA AGGAGTCC 3' | 22 | 22 | |
| Tr273wa3_F3 | 5' ATAACTATTTA AATAACGAAAG 3' | 40 | 40 | |
| Tr273wa4_F3 | 5' CAATAAATAAC TATTTAAATAAC 3' | 39 | 39 | |
| Tr273wa4_F3 | 5' CAATAAACAAC TATTTAAATAAC 3' | 2 | 2 | |
| Tr273wa_FIP | 5' GTCACACATGC TGTATTGTGttttC TATATTTGGCCTCT CTCCCT 3' | 21 | F1c 44c(84) | F2 42 |
| Tr273wa_BIP | 5' GCTGCAATGAG TCTAACGCAAtttt AATATGAGCCCAGA CCTA 3' | 23 | B1c 48 | B2 53c(89) |
| Tr273wa2_BIP | 5' GCTGCAATGAG TCTAACGCAAtttt ACAATATGAGCCCA GACC 3' | 24 | 48 | 50c(86) |

TABLE 3-continued

| Primer's name | Sequence | SEQ ID No. | Matching of FIG. 2 (SEQ ID No.) (c: complimentary sequence) | |
|---|---|---|---|---|
| Tr273wa3_BIP | 5' CTGCAATGAGT CTAACGCAACtttt TATGAGCCCAGACC TTTCG 3' | 25 | 47 | 52c(88) |
| Tr273wa4_BIP | 5' GCAATGAGTCT AACGCAACATAATA AACTCATGAGCCCA GACCTTTCG 3' | 26 | 46 | 51c(87) |
| Tr273wa5_BIP | 5' GCAATGAGTCT AACGCAACATAATA AACTCACAATATGA GCCCAGACC 3' | 27 | 46 | 50c(86) |
| Tr273wa_B3 | 5' CTGGCAAGATA TTGATACAACA 3' | 10 | 10 | |
| Tr273wa_LF | 5' AATTTTTTGAT TATCACGC 3' | 11 | 11 | |

The arrows in the figures show the direction of the sequences when used as primers. Each underlined base is a site modified according to mutation of the Guinea 14 strain.

Figure 3A:
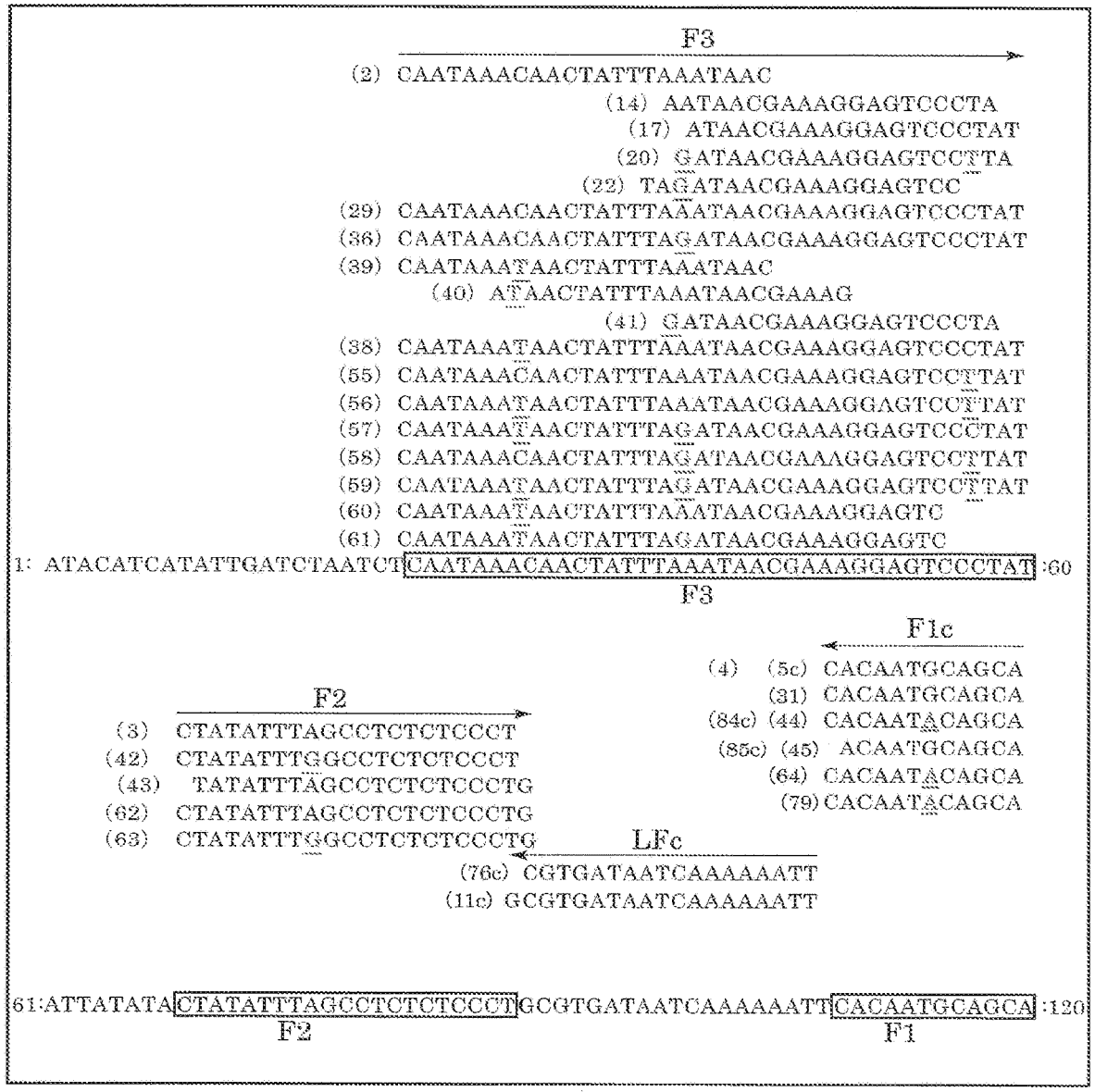
FIG. 3A is a view showing an example of cDNA of Zaire Ebola virus genome and each primer recognition region corresponding to the cDNA.

Further, similarly to FIGS. 2A to 2C, specific examples of the recognition sequence are shown in FIGS. 3A and 3B. SEQ ID numbers are provided in parentheses. A sequence represented by a SEQ ID number having a symbol "c" represents a complementary sequence. FIGS. 3A and 3B show the same sequences as the consensus sequences of FIGS. 2A to 2C (i.e., sequences 18299-18658 in the region of cDNA) as sequences at positions 1-360.

The recognition sequences included in the primer set of one of the embodiments may be, for example, as follows. The F3 sequence includes at least 13 consecutive bases included in SEQ ID NO: 29, 36, 38, 55, 56, 57, 58, 59, 60 or 61. The F2 sequence includes at least 13 consecutive bases included in SEQ ID NO: 62 or 63. The F1 sequence includes at least 13 consecutive bases included in SEQ ID NO: 31 or 64. The B1c sequence includes at least 13 consecutive bases included in SEQ ID NO: 68, 69, 70, 71, 72, 73, 74 or 75. The B2c sequence includes at least 13 consecutive bases included in SEQ ID NO: 65 or 66. The B3c sequence includes at least 13 consecutive bases included in SEQ ID NO: 34, 67, 82 or 83. These recognition sequences may be at least consecutive bases 15, 16, 17, 18, 19, 20, 21, 22, 23, 24, and 25 included in the SEQ ID NOS:, and may be, for example, 15 to 30 bases. Alternatively, the recognition sequences may be complementary sequences of the bases.

In order to amplify the Guinea 14 strain, it is important to design the BIP primer and select the F3 and B3 primers which are combined with the BIP primer. In order to amplify the Guinea 14 strain, it is important to design on SEQ ID NO: 75. For example, a preferred B1c sequence may be at least 13 consecutive bases so as to include consecutive bases from any of the bases at positions 1-5 from the 5' end which are included in SEQ ID NO: 75, or at least 13 consecutive bases so as to include consecutive bases from any of the bases at positions 1-6 from the 3' end. For example, a preferred B1c sequence is SEQ ID NO: 6, 32, 46, 47 or 48, and is more preferably SEQ ID NO: 46, 47 or 48.

For example, a preferred B2 region for amplifying the Guinea 14 strain is the region at positions 18493-18522 in the cDNA region corresponding to the trailer sequence.

For example, the B2c sequence may be designed based on the sequences represented by SEQ ID NOS: 65 and 66. For example, a preferred B2c sequence may be at least 13 consecutive bases so as to include consecutive bases from any of the bases at positions 1-7 from the 5' end which are included in SEQ ID NOS: 65 and 66. For example, a preferred B2c sequence is SEQ ID NO: 33, 50, 51, 52, 53 or 78, and is more preferably SEQ ID NO: 50, 51, 52 or 53. Alternatively, it is a complementary sequence of each SEQ ID number.

For example, a preferred F3 sequence is at least 13 consecutive bases included in SEQ ID NO: 29, 55, 60 or 61, and is more preferably at least 13 consecutive bases so as to include consecutive bases from any of the bases at positions 1-5 from the 5' end which are included in SEQ ID NO: 29, 55, 60 or 61. For example, the sequence is SEQ ID NO: 2, 39 or 40, and more preferably SEQ ID NO: 2 or 39. Alternatively, it is a complementary sequence of each SEQ ID number.

For example, a preferred F2 sequence is SEQ ID NO: 3, 42, 43, 62 or 63, and is more preferably SEQ ID NO: 3 or 42. Alternatively, it is a complementary sequence of each SEQ ID number.

For example, a preferred F1 sequence is SEQ ID NO: 4, 44, 45 or 79, and is more preferably SEQ ID NO: 4, 44 or 45. Alternatively, it is a complementary sequence of each SEQ ID number.

For example, a preferred B3c sequence may be at least 13 consecutive bases so as to include consecutive bases from any of the bases at positions 1-5 from the 5' end which are included in SEQ ID NO: 82, or at least 13 consecutive bases so as to include consecutive bases from any of the bases at positions 1-7 from the 3' end which are included in SEQ ID NO: 34. The preferred B3c sequence is, for example, SEQ ID NO: 9 or 19. Alternatively, it is a complementary sequence of each SEQ ID number.

The use of the loop primer enables amplification efficiency to be increased. For example, the sequence for a preferred loop primer is a sequence including the sequences represented by SEQ ID NOS: 11, 28, and 76, or a sequence including at least 13 consecutive bases of these sequences. SEQ ID NOS: 11 and 76 may be preferably used as an LFc primer. SEQ ID NOS: 28 and 77 may be preferably used as an LBc primer. Further, the sequence for the loop primer may be at least 15, 16, 17, 18, 19, 20, 21, 22, 23, 24 or 25 consecutive bases which are included in the SEQ ID NOS: and may be, for example, 15 to 30 bases. Alternatively, it may be a complementary sequence of each SEQ ID number.

In the preferred loop primer, for example, the LFc sequence is of SEQ ID NO: 76, and the LBc sequence is of SEQ ID NO: 77. Alternatively, the loop primers are of complementary sequences of the sequences.

Each of the primers may have a length of 13 to 40 bases, for example, 15 to 30 bases.

Each of the primer may include another sequence or a component, in addition to the recognition sequence as long as the annealing to the template is not inhibited and the primer extension is not prevented.

For example, the FIP primer may include a linker between the F1c sequence and the F2 sequence. Further, the BIP primer may include a linker between the B1 sequence and the B2c sequence. The linker sequence may be an arbitrary base sequence, and may be preferably a sequence which is not specifically bound to a template sequence. The linker sequence may have a length, for example, of 1 to 6 bases. A preferred linker sequence is, for example, TTTT.

For example, respective primers in a preferred primer set may be as follows. The F3 primer may include a sequence represented by SEQ ID NO: 2, 17, 20, 22 or 39 or a complementary sequence of the sequence. The FIP primer may include a sequence represented by SEQ ID NO: 12, 18 or 21 or a complementary sequence of the sequence. The BIP primer may include a sequence represented by SEQ ID NO: 13, 23, 24, 25, 26 or 27 or a complementary sequence of the sequence. The B3 primer may include a sequence represented by SEQ ID NO: 10 or 19 or a complementary sequence of the sequence.

Alternatively, respective primers in a preferred primer set may be, for example, as follows. The F3 primer may include a sequence represented by SEQ ID NO: 2, 17, 20, 22 or 39 or at least 13 consecutive bases which are included in a complementary sequence of them. The FIP primer may include a sequence represented by SEQ ID NO: 12, 18 or 21 or at least 13 consecutive bases which are included in a complementary sequence of them. The BIP primer may include a sequence represented by SEQ ID NO: 13, 23, 24, 25, 26 or 27 or at least 13 consecutive bases which are included in a complementary sequence of them. The B3 primer may include a sequence represented by SEQ ID NO: 10 or 19 or at least 13 consecutive bases which are included in a complementary sequence of them.

Each combination of sequences for F3, FIP, BIP, and B3 primers included in the primer set is selected from the group consisting of:

(1) a combination of SEQ ID NOS: 17, 18, 13, and 19;
(2) a combination of SEQ ID NOS: 22, 21, 15, and 10;
(3) a combination of SEQ ID NOS: 20, 21, 23, and 10;
(4) a combination of SEQ ID NOS: 22, 21, 24, and 10;
(5) a combination of SEQ ID NOS: 22, 21, 25, and 10;
(6) a combination of SEQ ID NOS: 22, 21, 26, and 10;
(7) a combination of SEQ ID NOS: 22, 21, 27, and 10;
(8) a combination of SEQ ID NOS: 20, 12, 23, and 10;
(9) a combination of SEQ ID NOS: 20, 12, 24, and 10;
(10) a combination of SEQ ID NOS: 20, 12, 25, and 10;
(11) a combination of SEQ ID NOS: 20, 12, 26, and 10;
(12) a combination of SEQ ID NOS: 20, 12, 27, and 10;
(13) a combination of SEQ ID NOS: 20, 12, 13, and 10;
(14) a combination of SEQ ID NOS: 20, 12, 13, and 19;
(15) a combination of SEQ ID NOS: 22, 12, 13, and 10;
(16) a combination of SEQ ID NOS: 22, 12, 13, and 19;
(17) a combination of SEQ ID NOS: 39, 12, 13, and 10;
(18) a combination of SEQ ID NO: 2, 12, 13, and 10; and
(19) a combination of complementary sequences of four sequences included in the combinations (1) to (18).

A more preferred primer set is a primer set including primers in the combinations (3), (4), (5), (6), (7), (8), (9), (10), (11), (12), (13), (14), (15), (16), (17), and (18).

Further, it is preferable that a loop primer is further included in the primer set. Each combination of sequences for F3, FIP, BIP, B3, and LFc primers included in the primer set may be

(20) a combination of SEQ ID NOS: 39, 12, 13, 10, and 11 or a combination of complementary sequences of five sequences included in the primer set;
or each combination of sequences for F3, FIP, BIP, B3 primers, and LBc loop primer included in the primer set may be
(21) a combination of SEQ ID NOS: 39, 12, 13, 10, and 28 or a combination of complementary sequences of five sequences included in the primer set;
or each combination of sequences for F3, FIP, BIP, B3, LFc loop, and LBc loop primers included in the primer set may be
(22) a combination of SEQ ID NOS: 39, 12, 13, 10, 11, and 28 or a combination of complementary sequences of six sequences included in the primer set or
(23) a combination of SEQ ID NOS: 2, 12, 13, 10, and 11 or a combination of complementary sequences of five sequences included in the primer set;
or each combination of sequences for F3, FIP, BIP, B3 primers, and LBc loop primer included in the primer set may be
(24) a combination of SEQ ID NOS: 2, 12, 13, 10, and 28 or a combination of complementary sequences of five sequences included in the primer set;
or each combination of sequences for F3, FIP, BIP, B3, LFc loop, and LBc loop primers included in the primer set may be
(25) a combination of SEQ ID NOS: 2, 12, 13, 10, 11, and 28 or a combination of complementary sequences of six sequences included in the primer set.

Further, it is preferable that each of the primer sets includes an LFc primer represented by SEQ ID NO: 76.

The sequences included in each of the primer sets may include sequences corresponding to recognition sequences for respective primer sequences. Further, as long as the annealing to the template is not inhibited and the primer extension is not prevented, each of the primers may include another sequence or a component, in addition to the recognition sequence.

The method allows for amplification of the gene of the Guinea 14 strain of the ZEBOV strain which could not be detected before. There is no conventional primer set capable of amplifying the gene of the Guinea 14 strain. Therefore, for example, in the case of being infected with the Guinea 14 strain, the result obtained by the conventional primer set is a false negative result. According to the primer set of one of the embodiments, it is possible to amplify the Guinea 14 strain. Thus, the amplified product is detected, thereby allowing for detection of ZEBOV with high accuracy compared to the conventional method. Further, the primer set can amplify the gene of the Guinea 14 strain in a short time. That is, for example, when $10^4$ copies of RNA are present, it is possible to perform amplification so as to detect the amplified products for about 20 minutes. This allows for rapid detection of the ZEBOV.

For example, the primer sets (17), (18), (20), (21), (22), (23), (24), and (25) can amplify not only the gene of the Guinea 14 strain but also the Zaire 76 strain and the Zaire 95 strain in a short time. Therefore, each of these primer sets is a most preferred primer set. Accordingly, it is possible to detect the ZEBOV accurately and rapidly.

According to another embodiment, there is provided a method of detecting the Guinea strain of ZEBOV. The method of detecting the Guinea strain of ZEBOV may include amplifying a nucleic acid included in a sample using any of the primer sets, detecting the amplified product, and determining whether the Guinea strain of ZEBOV is included in the sample.

The method of amplifying a nucleic acid may be any of the known methods themselves which amplify nucleic acids according to an LAMP method or the same principle as the LAMP method. In the method, a reverse transcription reaction may be performed prior to the nucleic acid amplification, or an RT-LAMP method performs the reverse transcription reaction and the amplification reaction as one reaction at a time may be used. In the method, a more preferred amplification method is the RT-LAMP method.

Further, the amplified product can be detected using, for example, turbidity or fluorescence as an indicator. The detection of the amplified product using turbidity as an indicator may be performed by a turbidimeter, an absorption spectrometer, visual observation or the like. The detection of the amplified product using fluorescence as an indicator may be performed by detecting the fluorescence generated using a reagent that produces fluorescence, such as a fluorescence reagent containing calcein or intercalater, depending on the presence of the amplified product or the amplification reaction.

The detection of the amplified product may be performed, for example, at a specific time after starting the amplification reaction. The step of determining whether the Guinea strain of ZEBOV is contained in a sample may be performed, for example, by determining whether the amplified product has a predetermined threshold or more at a specific time.

For example, in the case of using turbidity as an indicator, when a predetermined turbidity value or more is measured, it may be determined that the Guinea strain of ZEBOV is contained in the sample. For example, when a turbidity value of 0.1 or more is measured for duration of 60 minutes, it may be determined that the Guinea strain of ZEBOV is contained in a specimen.

The sample to be subjected to the method of detecting the Guinea strain of ZEBOV may be a sample that contains a nucleic acid or a sample that may contain a nucleic acid. The sample may be obtained from either the in vivo environment or the ex vivo environment. The sample is preferably in a state that does not block the amplification reaction and may be pretreated by any means known in itself after being extracted. Examples of the sample may include blood, plasma, serum, urine, feces, sperm, saliva, oral mucosa, coelomic membrane except oral mucosa, pharynx wiping liquid and sputum.

The method allows for detection of the Guinea 14 strain of the ZEBOV which has not been detected before. In other words, the amplified product obtained by the method is detected, thereby allowing for detection of ZEBOV with high accuracy compared to the conventional method. Further, the primer set can amplify the gene of the Guinea 14 strain in a short time. This allows for rapid detection of the ZEBOV.

Figure 4:
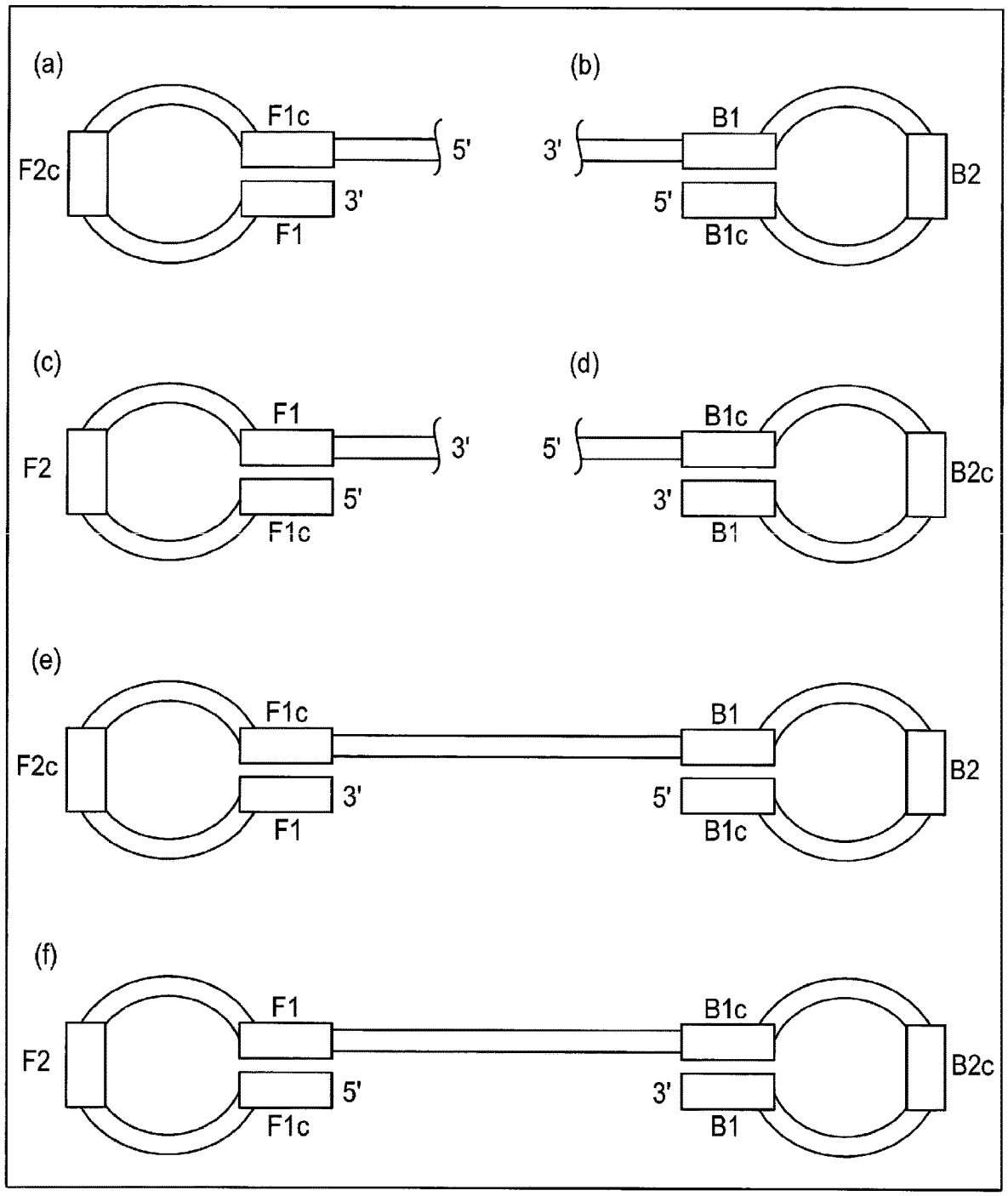
FIG. 4 shows pattern diagrams showing nucleic acid structures.

In the method, the nucleic acid structure shown in FIG. 4 is obtained as an amplified product or a part thereof. The presence of the nucleic acid structure is detected so that the Guinea 14 strain of ZEBOV (if desired, the Zaire 76 strain and the Zaire 95 strain) can be detected. The nucleic acid structure is also provided as an embodiment.

The nucleic acid structure will be described with reference to FIG. 4. FIGS. 4(a) to 4(d) show a stem-loop structure includes a stem portion that is a double-stranded region including mutually complementary sequences and a loop portion that is a single-stranded region formed by the double-stranded region.

The nucleic acid structure of FIG. 4(a) includes an F1 sequence, an F2c sequence, and an F1c sequence from the 3' side toward the 5' side in this order. The F1 sequence is bound to the F1c sequence to form a double-strand.

The nucleic acid structure of FIG. 4(b) includes a B1 sequence, a B2 sequence, and a B1c sequence from the 3' side toward the 5' side in this order. The B1 sequence is bound to the B1c sequence to form a double-strand.

The nucleic acid structure of FIG. 4(c) includes an F1c sequence, an F2 sequence, and an F1 sequence from the 3' side toward the 5' side in this order. The F1c sequence is bound to the F1 sequence to form a double-strand.

The nucleic acid structure of FIG. 4(d) includes a B1c sequence, a B2c sequence, and a B1 sequence from the 3' side toward the 5' side in this order. The B1c sequence is bound to the B1 sequence to form a double-strand.

FIGS. 4(e) and 4(f) show a dumbbell structure having stem loop structures at the 3' and 5' sides.

The nucleic acid structure of FIG. 4(e) includes an F1 sequence, an F2c sequence, an F1c sequence, a B1 sequence, a B2 sequence, and a B1 sequence from the 3' side toward the 5' side in this order. The F1 sequence is bound to the F1c sequence to form a double-strand, and the B1 sequence is bound to the B1c sequence to form a double-strand.

The nucleic acid structure of FIG. 4(f) includes an F1c sequence, an F2 sequence, an F1 sequence, a B1c sequence, a B2c sequence, and a B1 sequence from the 3' side toward the 5' side in this order. The F1c sequence is bound to the F1 sequence to form a double-strand, and the B1c sequence is bound to the B1 sequence to form a double-strand.

The sequences included in these nucleic acid structures are determined according to sequences of primer sets used for amplification reaction. That is, the primer sets are provided, whereby the nucleic acid structures are obtained for the first time. Detection of the nucleic acid structures allows for detection of the Guinea 14 strain of ZEBOV which would not have been detected. Thus, it is possible to detect the ZEBOV with high accuracy compared to the conventional method. The nucleic acid structures can be rapidly formed by using the primer sets. Therefore, the nucleic acid structures may be used to rapidly detect the ZEBOV.

According to one of the embodiments, there is provided an assay kit that is used in the method of detecting ZEBOV. The assay kit may include any of the primer sets. Further, the assay kit may include a container that accommodates a primer set, an enzyme for performing an amplification reaction, a substrate, a cleaning solution, a buffer solution and/or salts for preparing the buffer solution.

The assay kit allows for detection of the Guinea 14 strain of ZEBOV which could not be detected before.

Thus, it is possible to detect the ZEBOV with high accuracy compared to the conventional method. Further, the use of the assay kit allows for amplification of the gene of the Guinea 14 strain in a short time. This allows for rapid detection of the ZEBOV.

EXAMPLES

Tests for detecting ZEBOV were performed using the primer set of each of the embodiments.

(1) Viral RNA Synthesis

The ZEBOV of the Zaire 76 strain or the Zaire 95 strain was used in the experiment. Viral RNAs of the Zaire 76 strain and the Zaire 95 strain were given from National Microbiological Laboratory, Public Health Agency of Canada. A part of the viral cDNA including a primer design region was amplified by RT-PCR and purified. In the case of the Guinea 14 strain, a part of the viral cDNA (300 bases) including a primer design region was synthesized (Hokkaido System Science Co., Ltd., Japan, Sapporo). The cDNA was cloned into a pGEM3Zf(+) vector (Promega). A partial viral RNA including a primer design region was synthesized using a T7 RNA polymerase and purified. The viral RNA was quantified by spectrophotometry.

In order to detect the Zaire Ebola virus, the primer sets shown in Table 4 were provided. In each table, Primer Set No. was shown in the "Set ID" column.

TABLE 4

| Set ID | Primer's name | Sequence | SEQ ID No. |
|---|---|---|---|
| 1 | Tr273_F3 | AATAACGAAAGGAGTCCCTA | 14 |
|   | Tr273_FIP | GTCACACATGCTGCATTGTGttttCTATATTTAGCCTCTCTCCCT | 12 |
|   | Tr273_BIP | GCCGCAATGAATTTAACGCAAttttAATATGAGCCCAGACCTT | 15 |
|   | Tr273_B3 | CTGACAGGATATTGATACAACA | 16 |
| 2 | Tr2_F3 | ATAACGAAAGGAGTCCCTAT | 17 |
|   | Tr2_FIP | TGTCACACATGCTGCATTGTttttTATATTTAGCCTCTCTCCCTG | 18 |
|   | Tr2_BIP | AACGCAACATAATAAACTCTGCAttttATCAATAACAATATGAGCCCAG | 13 |
|   | Tr2_B3 | CACTATTCCATCTGACAGGA | 19 |
| 3 | Tr273wa_F3 | GATAACGAAAGGAGTCCTTA | 20 |
|   | Tr273wa_FIP | GTCACACATGCTGTATTGTGttttCTATATTTGGCCTCTCTCCCT | 21 |
|   | Tr273_BIP | GCCGCAATGAATTTAACGCAAttttAATATGAGCCCAGACCTT | 15 |
|   | Tr273wa_B3 | CTGGCAAGATATTGATACAACA | 10 |
| 4 | Tr273wa2_F3 | TAGATAACGAAAGGAGTCC | 22 |
|   | Tr273wa_FIP | GTCACACATGCTGTATTGTGttttCTATATTTGGCCTCTCTCCCT | 21 |
|   | Tr273_BIP | GCCGCAATGAATTTAACGCAAttttAATATGAGCCCAGACCTT | 15 |
|   | Tr273wa_B3 | CTGGCAAGATATTGATACAACA | 10 |
| 5 | Tr273wa_F3 | GATAACGAAAGGAGTCCTTA | 20 |
|   | Tr273wa_FIP | GTCACACATGCTGTATTGTGttttCTATATTTGGCCTCTCTCCCT | 21 |
|   | Tr273wa_BIP | GCTGCAATGAGTCTAACGCAAttttAATATGAGCCCAGACCTA | 23 |
|   | Tr273wa_B3 | CTGGCAAGATATTGATACAACA | 10 |

TABLE 4-continued

| Set ID | Primer's name | Sequence | SEQ ID No. |
|---|---|---|---|
| 6 | Tr273wa2_F3 | TAGATAACGAAAGGAGTCC | 22 |
|   | Tr273wa_FIP | GTCACACATGCTGTATTGTGttttCTATATTTGGCCTCTCTCCCT | 21 |
|   | Tr273wa2_BIP | GCTGCAATGAGTCTAACGCAAttttACAATATGAGCCCAGACC | 24 |
|   | Tr273wa_B3 | CTGGCAAGATATTGATACAACA | 10 |
| 7 | Tr273wa2_F3 | TAGATAACGAAAGGAGTCC | 22 |
|   | Tr273wa_FIP | GTCACACATGCTGTATTGTGttttCTATATTTGGCCTCTCTCCCT | 21 |
|   | Tr273wa3_BIP | CTGCAATGAGTCTAACGCAACttttTATGAGCCCAGACCTTTCG | 25 |
|   | Tr273wa_B3 | CTGGCAAGATATTGATACAACA | 10 |
| 8 | Tr273wa2_F3 | TAGATAACGAAAGGAGTCC | 22 |
|   | Tr273wa_FIP | GTCACACATGCTGTATTGTGttttCTATATTTGGCCTCTCTCCCT | 21 |
|   | Tr273wa4_BIP | GCAATGAGTCTAACGCAACATAATAAACTC-ATGAGCCCAGACCTTTCG | 26 |
|   | Tr273wa_B3 | CTGGCAAGATATTGATACAACA | 10 |
| 9 | Tr273wa2_F3 | TAGATAACGAAAGGAGTCC | 22 |
|   | Tr273wa_FIP | GTCACACATGCTGTATTGTGttttCTATATTTGGCCTCTCTCCCT | 21 |
|   | Tr273wa5_BIP | GCAATGAGTCTAACGCAACATAATAAACTC-ACAATATGAGCCCAGACC | 27 |
|   | Tr273wa_B3 | CTGGCAAGATATTGATACAACA | 10 |
| 10 | Tr273wa_F3 | GATAACGAAAGGAGTCCTTA | 20 |
|   | Tr273_FIP | GTCACACATGCTGCATTGTGttttCTATATTTAGCCTCTCTCCCT | 12 |
|   | Tr273_BIP | GCCGCAATGAATTTAACGCAAttttAATATGAGCCCAGACCTT | 15 |
|   | Tr273wa_B3 | CTGGCAAGATATTGATACAACA | 10 |
| 11 | Tr273wa_F3 | GATAACGAAAGGAGTCCTTA | 20 |
|   | Tr273_FIP | GTCACACATGCTGCATTGTGttttCTATATTTAGCCTCTCTCCCT | 12 |
|   | Tr273wa_BIP | GCTGCAATGAGTCTAACGCAAttttAATATGAGCCCAGACCTA | 23 |
|   | Tr273wa_B3 | CTGGCAAGATATTGATACAACA | 10 |
| 12 | Tr273wa_F3 | GATAACGAAAGGAGTCCTTA | 20 |
|   | Tr273_FIP | GTCACACATGCTGCATTGTGttttCTATATTTAGCCTCTCTCCCT | 12 |
|   | Tr273wa2_BIP | GCTGCAATGAGTCTAACGCAAttttACAATATGAGCCCAGACC | 24 |
|   | Tr273wa_B3 | CTGGCAAGATATTGATACAACA | 10 |
| 13 | Tr273wa_F3 | GATAACGAAAGGAGTCCTTA | 20 |
|   | Tr273_FIP | GTCACACATGCTGCATTGTGttttCTATATTTAGCCTCTCTCCCT | 12 |
|   | Tr273wa3_BIP | CTGCAATGAGTCTAACGCAACttttTATGAGCCCAGACCTTTCG | 25 |
|   | Tr273wa_B3 | CTGGCAAGATATTGATACAACA | 10 |
| 14 | Tr273wa_F3 | GATAACGAAAGGAGTCCTTA | 20 |
|   | Tr273_FIP | GTCACACATGCTGCATTGTGttttCTATATTTAGCCTCTCTCCCT | 12 |
|   | Tr273wa4_BIP | GCAATGAGTCTAACGCAACATAATAAACTC-ATGAGCCCAGACCTTTCG | 26 |
|   | Tr273wa_B3 | CTGGCAAGATATTGATACAACA | 10 |
| 15 | Tr273wa_F3 | GATAACGAAAGGAGTCCTTA | 20 |
|   | Tr273_FIP | GTCACACATGCTGCATTGTGttttCTATATTTAGCCTCTCTCCCT | 12 |
|   | Tr273wa5_BIP | GCAATGAGTCTAACGCAACATAATAAACTC-ACAATATGAGCCCAGACC | 27 |
|   | Tr273wa_B3 | CTGGCAAGATATTGATACAACA | 10 |
| 16 | Tr273wa_F3 | GATAACGAAAGGAGTCCTTA | 20 |
|   | Tr273_FIP | GTCACACATGCTGCATTGTGttttCTATATTTAGCCTCTCTCCCT | 12 |
|   | Tr2_BIP | AACGCAACATAATAAACTCTGCAttttATCAATAACAATATGAGCCCAG | 13 |
|   | Tr273wa_B3 | CTGGCAAGATATTGATACAACA | 10 |
| 17 | Tr273wa_F3 | GATAACGAAAGGAGTCCTTA | 20 |
|   | Tr273_FIP | GTCACACATGCTGCATTGTGttttCTATATTTAGCCTCTCTCCCT | 12 |
|   | Tr2_BIP | AACGCAACATAATAAACTCTGCAttttATCAATAACAATATGAGCCCAG | 13 |
|   | Tr2_B3 | CACTATTCCATCTGACAGGA | 19 |
| 18 | Tr273wa2_F3 | TAGATAACGAAAGGAGTCC | 22 |
|   | Tr273_FIP | GTCACACATGCTGCATTGTGttttCTATATTTAGCCTCTCTCCCT | 12 |
|   | Tr2_BIP | AACGCAACATAATAAACTCTGCAttttATCAATAACAATATGAGCCCAG | 13 |
|   | Tr273wa_B3 | CTGGCAAGATATTGATACAACA | 10 |
| 19 | Tr273wa2_F3 | TAGATAACGAAAGGAGTCC | 22 |
|   | Tr273_FIP | GTCACACATGCTGCATTGTGttttCTATATTTAGCCTCTCTCCCT | 12 |
|   | Tr2_BIP | AACGCAACATAATAAACTCTGCAttttATCAATAACAATATGAGCCCAG | 13 |
|   | Tr2_B3 | CACTATTCCATCTGACAGGA | 19 |
| 20 | Tr273wa4_F3 | CAATAAATAACTATTTAAATAAC | 39 |
|   | Tr273_FIP | GTCACACATGCTGCATTGTGttttCTATATTTAGCCTCTCTCCCT | 12 |
|   | Tr2_BIP | AACGCAACATAATAAACTCTGCAttttATCAATAACAATATGAGCCCAG | 13 |
|   | Tr273wa_B3 | CTGGCAAGATATTGATACAACA | 10 |

TABLE 4-continued

| Set ID | Primer's name | Sequence | SEQ ID No. |
|---|---|---|---|
| 21 | Tr273wa4_F3 | CAATAAATAACTATTTAAATAAC | 39 |
|  | Tr273_FIP | GTCACACATGCTGCATTGTGttttCTATATTTAGCCTCTCTCCCT | 12 |
|  | Tr2_BIP | AACGCAACATAATAAACTCTGCAttttATCAATAACAATATGAGCCCAG | 13 |
|  | Tr273wa_B3 | CTGGCAAGATATTGATACAACA | 10 |
|  | Tr273wa_LF | AATTTTTTGATTATCACGC | 11 |
| 22 | Tr273wa4_F3 | CAATAAATAACTATTTAAATAAC | 39 |
|  | Tr273_FIP | GTCACACATGCTGCATTGTGttttCTATATTTAGCCTCTCTCCCT | 12 |
|  | Tr2_BIP | AACGCAACATAATAAACTCTGCAttttATCAATAACAATATGAGCCCAG | 13 |
|  | Tr273wa_B3 | CTGGCAAGATATTGATACAACA | 10 |
|  | Tr2_LB | CTCTTTATAATTAAGCTTTAACG | 28 |
| 23 | Tr273wa4_F3 | CAATAAATAACTATTTAAATAAC | 39 |
|  | Tr273_FIP | GTCACACATGCTGCATTGTGttttCTATATTTAGCCTCTCTCCCT | 12 |
|  | Tr2_BIP | AACGCAACATAATAAACTCTGCAttttATCAATAACAATATGAGCCCAG | 13 |
|  | Tr273wa_B3 | CTGGCAAGATATTGATACAACA | 10 |
|  | Tr273wa_LF | AATTTTTTGATTATCACGC | 11 |
|  | Tr2_LB | CTCTTTATAATTAAGCTTTAACG | 28 |
| 24 | Tr273_F3 | AATAACGAAAGGAGTCCCTA | 14 |
|  | Tr273_FIP | GTCACACATGCTGCATTGTGttttCTATATTTAGCCTCTCTCCCT | 12 |
|  | Tr2_BIP | AACGCAACATAATAAACTCTGCAttttATCAATAACAATATGAGCCCAG | 13 |
|  | Tr273_B3 | CTGACAGGATATTGATACAACA | 16 |
| 25 | Tr273_F3 | AATAACGAAAGGAGTCCCTA | 14 |
|  | Tr273_FIP | GTCACACATGCTGCATTGTGttttCTATATTTAGCCTCTCTCCCT | 12 |
|  | Tr2_BIP | AACGCAACATAATAAACTCTGCAttttATCAATAACAATATGAGCCCAG | 13 |
|  | Tr273_B3 | CTGACAGGATATTGATACAACA | 16 |
|  | Tr273wa_LF | AATTTTTTGATTATCACGC | 11 |

(2) Confirmation of Reactivity of Primer Set

Each of the primer sets shown in the paragraph (1) was used to perform LAMP amplification in the following manner. The composition of an LAMP reaction solution for amplifying a nucleic acid by the LAMP method is as follows.

The RT-LAMP reaction was performed in accordance with the protocol of manufacturer of LoopampRNA amplification kit (Eiken Chemical Co., Ltd., Japan, Tokyo).

| Composition of the LAMP reaction solution (25 μL) | |
|---|---|
| FIP | 40 pmol |
| BIP | 40 pmol |
| F3 | 5 pmol |
| B3 | 3 pmol |
| LF | 20 pmol |
| LB | 20 pmol |
| 2 x Reaction Mixture | 12.5 μL |
| Enzyme Mix (Bst DNA polymerase, avian myeloblastosis virus reverse transcriptase) | 1.0 μL |
| RNA sample | 2.0 μL. |

The amounts of synthetic RNAs used for the reaction were $6.4 \times 10^4$ copies for Zaire 76 strain, $3.9 \times 10^4$ copies for Zaire 95 strain, and $6.1 \times 10^4$ copies for Guinea 14 strain.

In order to perform real-time monitoring of amplification by RT-LAMP assay, the LAMP reaction solution was incubated at 63° C. and observed by absorption spectrophotometry using a real-time turbidimeter (LA-200; Teramecs, Kyoto, Japan).

A test was performed according to the same protocol as described above except that water was added in place of the RNA sample, in conjunction with the amplification using each of the primer sets and the measurement of turbidity, and the result was used as a negative control.

The results are shown in Table 5.

TABLE 5

| | Time required for amplification and detection (min) | | |
|---|---|---|---|
| Set ID | Zaire76 | Zaire95 | Guinea14 |
| 1 | 32.4 | 23.8 | ND |
| 2 | 27.1 | 28.1 | 53.1 |
| 3 | | | ND |
| 4 | | | 48.8 |
| 5 | ND | | 23.4 |
| 6 | | | 23.7 |
| 7 | | | 27.3 |
| 8 | | | 24.7 |
| 9 | | | 26.4 |
| 10 | | 23.3 | ND |
| 11 | | ND | 24.6 |
| 12 | | ND | 24.7 |
| 13 | | 45.7 | 28.6 |
| 14 | | 33.3 | 27.7 |
| 15 | | 33.5 | 27.6 |
| 16 | | 24.7 | 27.9 |
| 17 | | 23.1 | 30 |
| 18 | | 25.1 | 28.8 |
| 19 | | 23.6 | 30.7 |
| 20 | 36.2 | | 35 |
| 21 | 27.4 | | 24.9 |
| 22 | 38.7 | | 36.6 |
| 23 | 27.8 | | 26.2 |
| 24 | 32.2 | | ND |
| 25 | 24.7 | | 36.8 |

Table 5 shows the results obtained by amplifying the Zaire 76 strain, the Zaire 95 strain or the Guinea 14 strain by the RT-LAMP method using each of the primer sets shown in Table 4 and detecting the amplified products using turbidity as an indicator. In each result, the time required for allowing the turbidity to reach 0.1 or more was designated in minutes. A turbidity threshold of 0.1 or more was set based on the turbidity obtained from a plurality of negative controls. That is, the threshold is a value obtained by doubling the average of the turbidity values obtained from the negative controls. In each table, Primer Set Number was shown in the "Set ID" column.

The results are as follows. A turbidity value of 0.1 or more (i.e., a threshold) was not observed in Primer Set Nos. 1, 3, 10, and 24.

A turbidity value of 0.1 or more was observed within 40 minutes in Primer Set Nos. 5, 6, 7, 8, 9, 11, 12, 13, 14, 15, 16, 17, 18, 19, 21, and 23. Further, a turbidity value of 0.1 or more was observed in 25 minutes in Primer Set Nos. 5, 6, 7, 8, 9, 11, 12, 21, and 23.

Furthermore, a turbidity value of 0.1 or more was observed in 35 minutes in Primer Set No. 20. To this primer set, Tr273 wa_LF was added as an LFc loop primer represented by SEQ ID NO: 11. As a result, in the case of Primer Set No. 21, the amplification efficiency was increased and a turbidity value of 0.1 or more was observed in about 25 minutes. Further, in the case of the primer set 23 obtained by adding an LBc loop primer represented by SEQ ID NO: 28 and an LFc loop primer represented by SEQ ID NO: 11 to Primer Set No. 20, the amplification efficiency was increased and a turbidity value of 0.1 or more was observed in about 26.2 minutes. On the other hand, in the case of Primer Set 22 including Primer Set No. 20 having an LBc loop primer represented by SEQ ID NO: 28 (i.e., Tr2_LB) added thereto, the amplification efficiency was not affected.

Based on these results, a turbidity value of 0.1 or more was observed within 40 minutes in Primer Set Nos. 5, 6, 7, 8, 9, 11, 12, 13, 14, 15, 16, 17, 18, 19, 21, and 23. Thus, these are examples of preferred primer sets.

(3) Influence of Combination of Primers on Amplification of Guinea 14 Strain

Among the primer sets shown in the paragraph (1), Primer Set Nos. 1, 2, 5, 20, and 22 and the loop primer represented by SEQ ID NO: 11 or 28 were used to perform a test according to the same protocol as described in the paragraph (2).

The results are shown in FIGS. 5A to 5L. FIGS. 5A to 5L show the results obtained by measuring the reactivity when used each of the primer sets with the lapse of time using turbidity as an indicator. In each graph, the time (in minutes) was plotted on a horizontal axis and the turbidity was plotted on a vertical axis. As for the data in each graph, a solid line represents the result of amplification of the Zaire 76 strain and a dashed line represents the result of amplification of the Guinea 14 strain. In all the data, the turbidity of each of the negative controls was measured, in addition to the amplification by each of the primer sets.

Figure 5G:
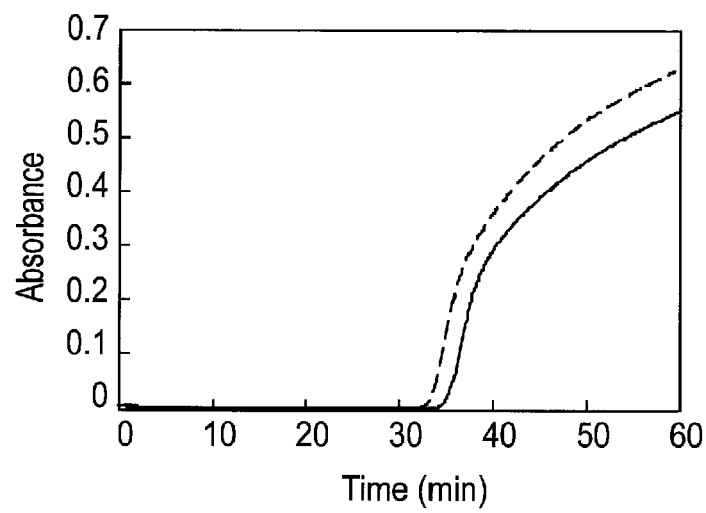
FIG. 5G is a graph showing the experimental results.
Figure 5H:
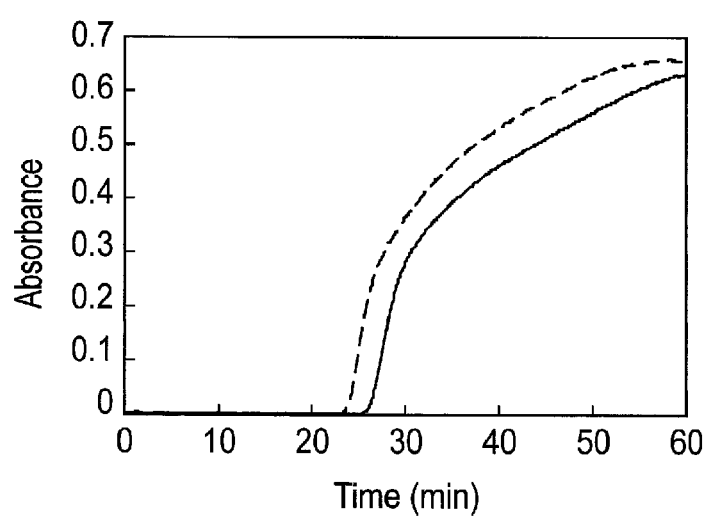
FIG. 5H is a graph showing the experimental results.
Figure 5I:
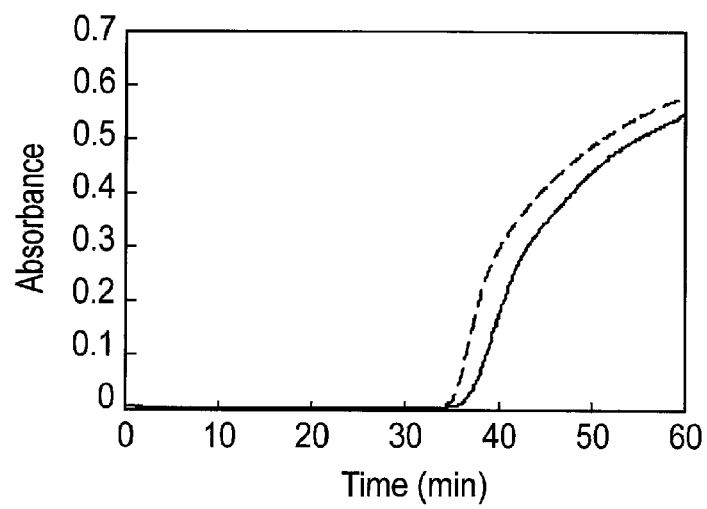
FIG. 5I is a graph showing the experimental results.
Figure 5J:
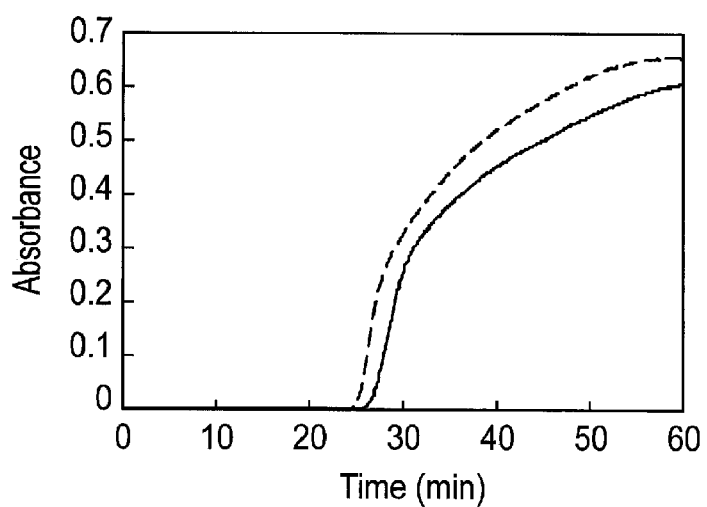
FIG. 5J is a graph showing the experimental results.

FIG. 5A shows the result obtained by using Primer Set No. 1, FIG. 5B shows the result obtained by using Primer Set No. 1' produced by adding an LFc primer to Primer Set No. 1, FIG. 5C shows the result obtained by using Primer Set No. 2, FIG. 5D shows the result obtained by using Primer Set No. 2' produced by adding an LBc primer to Primer Set No. 2, FIG. 5E shows the result obtained by using Primer Set No. 5, FIG. 5F shows the result obtained by using Primer Set No. 5' produced by adding an LFc primer to Primer Set No. 5, FIG. 5G shows the result obtained by using Primer Set No. 20, FIG. 5H shows the result obtained by using Primer Set No. 21, FIG. 5I shows the result obtained by using Primer Set No. 22, FIG. 5J shows the result obtained by using Primer Set No. 23, FIG. 5K shows the result obtained by using Primer Set No. 24, FIG. 5L shows the result obtained by using Primer Set No. 25.

In order to test all the primer sets, the turbidity of the negative control prepared by adding an RNA sample in place of water was measured. In any of the cases of the primer sets, the turbidity was approximately 0 at any time during measurement for 0 to 60 min.

As shown in FIG. 5A, in the case of Primer Set No. 1, the amplification of the Zaire 76 strain was started in about 30 minutes. However, the amplification of the Guinea strain was not observed. FIG. 5B shows the result when an LFc primer was added to this primer set. The addition of the LFc primer accelerated the amplification of the Zaire 76 strain, however, the amplification of the Guinea strain was not observed.

In the case of Primer Set No. 2, the amplification of the Zaire 76 strain was observed in about 25 minutes. Nearly about 50 minutes passed, finally, the amplification of the Guinea strain was observed (FIG. 5C). In the case of adding an LBc primer to Primer Set No. 2, the time for starting the amplification of the Zaire 76 strain was hardly changed. However, the start of the amplification of the Guinea strain was observed about 5 minutes earlier (FIG. 5D).

In the case of Primer Set No. 5, the amplification of the Guinea strain was observed in about 28 minutes (FIG. 5E). In the case of adding an LFc primer to Primer Set No. 5, the start of the amplification of Guinea was observed about 8 minutes earlier (FIG. 5F). Regardless of the presence or absence of the LFc primer, the start of the amplification of the Zaire 76 strain was not observed.

In the case of Primer Set No. 20, the amplification of the Guinea strain was observed in about 33 minutes, and the amplification of the Zaire 76 strain was observed in about 35 minutes (FIG. 5G). In the case of Primer Set No. 21 produced by adding an LFc primer to Primer Set No. 20, the amplification of the Guinea strain was observed in about 23 minutes, and the amplification of the Zaire 76 strain was observed in about 26 minutes (FIG. 5H).

In the case of Primer Set No. 22 produced by adding an LBc primer to Primer Set No. 20, as compared to Primer Set No. 20, a slight decrease in amplification efficiency was observed in the Guinea strain and the Zaire 76 strain (FIG. 5I).

In the case of Primer Set No. 23 produced by adding LFc and LBc primers to Primer Set No. 20, the amplification of the Guinea strain was observed in about 24 minutes, and the amplification of the Zaire 76 strain was observed in about 26 minutes (FIG. 5J).

In the case of Primer Set No. 24, the time for starting the amplification of the Zaire 76 strain was about 30 minutes, however, the amplification of the Guinea strain was not observed (FIG. 5K). In the case of Primer Set No. 25, the time required for the start of the amplification of the Zaire 76 strain was about 23 minutes, and the time required for the start of the amplification of the Guinea strain was about 35 minutes (FIG. 5L).

These results suggest that, in the primer sets, the LBc primer does not improve the amplification efficiency, and although the primer may be included, it is more preferable to use the LFc primer.

In the case of Primer Set No. 20, the start of the amplification of the Guinea 14 strain was observed in about 35 minutes, while in the case of Primer Set No. 24, the start of the amplification of the Guinea strain was not observed within 60 minutes. FIP primers and BIP primers in Primer Set Nos. 20 and 24 are respectively identical to each other. F3 primers in Primer Set Nos. 20 and 24 share six bases on the trailer sequence of ZEBOV and are sequences located close to each other. Further, B3 primers in Primer Set Nos.

20 and 24 are sequences sharing the same structure except that they have only two different types of bases.

Meanwhile, F3 primers, FIP primers, and B3 primers in Primer Set Nos. 6 and 8 are respectively identical to each other, and only BIP primers are different from each other. The type of bases selected for the mutation sites which are contained in the BIP primers in Primer Set Nos. 6 and 8 are different from each other. Even in such a situation, in the case of Primer Set Nos. 6 and 8, the amplification of the Guinea 14 strain of ZEBOV was similarly started in about 20 minutes.

When Primer Set No. 10 is compared to each of Primer Set Nos. 13 to 16, F3 primers, FIP primers, and B3 primers are respectively identical to each other, and only BIP primers are different from each other. The BIP primer in Primer Set No. 10 includes SEQ ID NO: 49 as a B1c sequence, and SEQ ID NO: 90 (a complementary sequence of SEQ ID NO: 54) as a B2 sequence. On the other hand, the BIP primer in Primer Set No. 13 includes SEQ ID NO: 47 as a B1c sequence and SEQ ID NO: 88 (a complementary sequence of SEQ ID NO: 52) as a B2 sequence. The BIP primer in Primer Set No. 14 includes SEQ ID NO: 46 as a B1c sequence and SEQ ID NO: 87 (a complementary sequence of SEQ ID NO: 51) as a B2 sequence. The BIP primer in Primer Set No. 15 includes SEQ ID NO: 46 as a B1c sequence and SEQ ID NO: 86 (a complementary sequence of SEQ ID NO: 50) as a B2 sequence. The BIP primer of Primer Set No. 16 includes SEQ ID NO: 6 as a B1c sequence and SEQ ID NO: 8 (a complementary sequence of SEQ ID NO: 7) as a B2 sequence. Particularly, F3 primers, FIP primers, and B3 primers in Primer Set Nos. 10 and 16 were designed so as to correspond to mutation sites of the Guinea 14 strain. There was a case in which a rapid amplification of the Guinea 14 strain was achieved depending on the BIP primer to be used (Primer Set Nos. 13 to 16), and there was a case in which the amplification of the Guinea 14 strain was not observed (Primer Set No. 10).

From these results, it is found that the design of the BIP primer is important to amplify the Guinea 14 strain. This result suggests that it is not possible to amplify the gene of the Guinea 14 strain by just selecting stored regions and allowing the primer sequence to be matched to the base of the mutation site of the gene of a new strain (i.e., Guinea 14 strain).

Further, when Primer Set Nos. 20 and 21 are compared to Primer Set Nos. 24 and 25, FIP primers and BIP primers in these four primer sets have in common. Further, F3 primers and B3 primers in Primer Set Nos. 20 and 21 are respectively identical, and F3 primers and B3 primers in Primer Set Nos. 24 and 25 are respectively identical. Further Primer Set Nos. 21 and 25 include the same LF primer. The experimental results of Primer Set Nos. 20, 21, 24, and 25 are shown in FIGS. 5G, 5H, 5K, and 5L, respectively. When FIG. 5G is compared to FIG. 5K, as indicated by the solid line, the time required for the start of the amplification of the Zaire 76 strain in FIG. 5G and the time required for the start of the amplification of the Zaire 76 strain in FIG. 5K are about 34 minutes and about 31 minutes, respectively. When the same LF primer was added to the primer sets, the start of the amplification of both the strains was observed less than 10 minutes earlier. On the other hand, as for the Guinea 14 strain indicated by the dashed line in each figure, Primer Set No. 20 (FIG. 5G) was compared to Primer Set No. 25 (FIG. 5K). In the former case, the start of the amplification was observed in about 32 minutes earlier than the case of the Zaire 76 strain. In the latter case, the start of the amplification of the Guinea 14 strain was not observed within 60 minutes. The LF primer was added to the primer sets, and then the start of the amplification of the Guinea 14 strain was observed about 10 minutes earlier in Primer Set No. 21, and the start of the amplification of the Zaire 76 strain was observed about 8 minutes earlier. On the other hand, the start of the amplification of the Zaire 76 strain was observed about 7 minutes earlier in Primer Set No. 25. Further, the start of the amplification of the Guinea 14 strain which had not been observed within 60 minutes was observed in about 33 minutes in Primer Set No. 25 with using the LF primer. These results show that the LF primer is an example of a preferred primer in the amplification of the Guinea 14 strain. On the other hand, a primer set preferred for amplification of ZEBOV and detection thereof is considered to be Primer Set No. 20 which could amplify the Guinea 14 strain efficiently and amplify the Zaire 76 strain, similarly to the Guinea 14 strain regardless of the presence of the use of the preferred primer. Further, a difference between Primer Set Nos. 24 and 21 is the F3 primer and the B3 primer. Taking into consideration other results described above, it is suggested that the design and selection of the F3 and B3 primers are important for the amplification of ZEBOV, particularly the amplification of the Guinea 14 strain.

(4) Influence of Loop Primer on Reactivity

Figure 6:
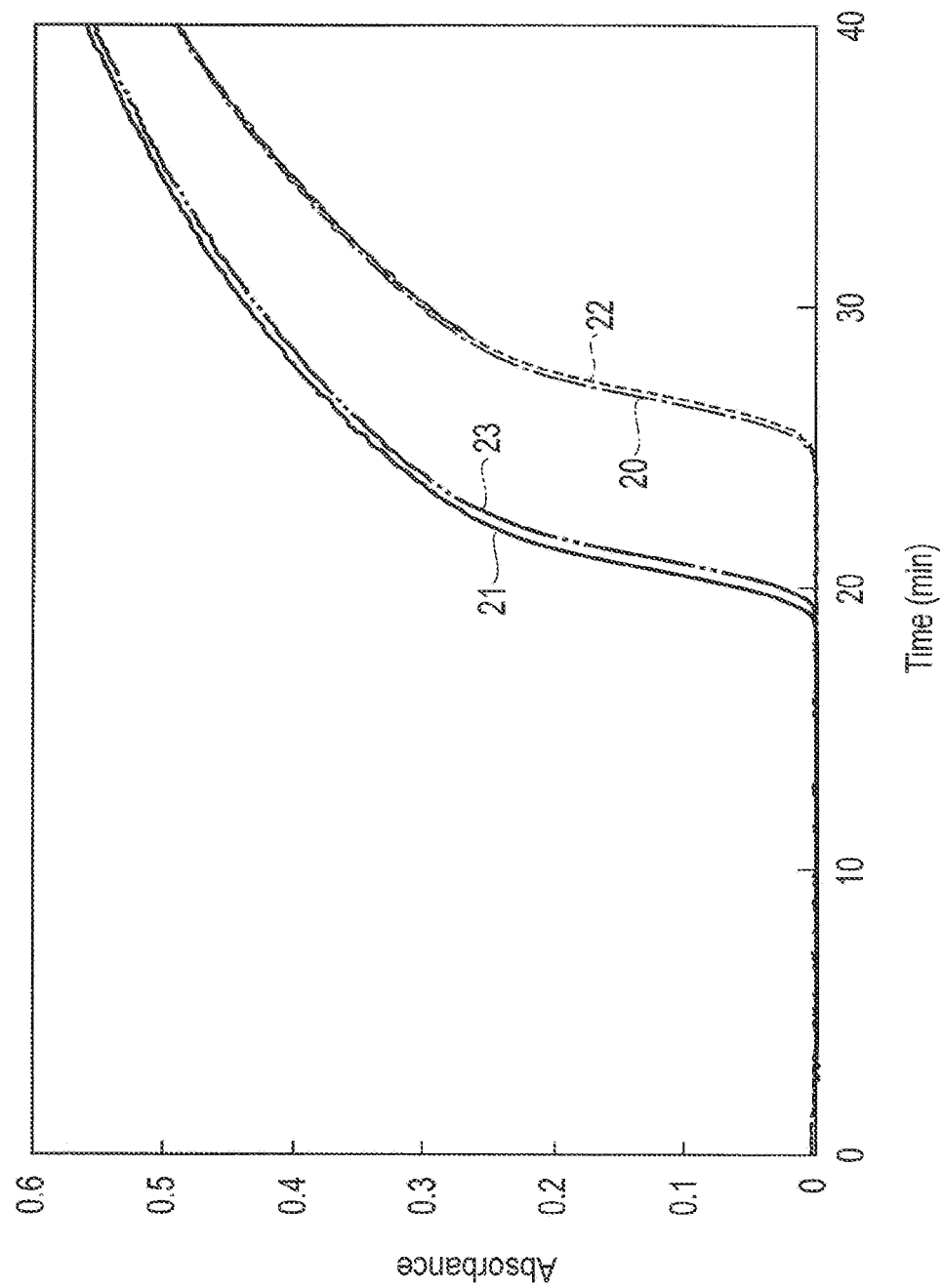
FIG. 6 is a graph showing the experimental results.

The RT-LAMP reaction was performed in the same manner as in the paragraph (2) except that the amount of synthetic RNA used for the LAMP reaction was $6.4 \times 10^5$ of Zaire 76 strain. Primer sets represented by Primer Set Nos. 20 to 23 were used. The results are shown in FIG. 6. The start of the amplification of the Zaire 76 strain was observed in about 25 minutes in Primer Set No. 20.inn The addition of the LFc primer allowed the time required for the start of the amplification to be shortened by about 5 minutes or more (Primer Set No. 21). In the case of adding the LBc primer to Primer Set No. 20, the time until when the amplification started was hardly changed (Primer Set No. 22). The result obtained by adding LFc and LBc primers to Primer Set No. 20 was nearly equal to the result obtained by adding only the LFc primer. This suggests that the LBc primer does not affect the amplification efficiency of the Guinea 14 strain.

The Guinea 14 strain of ZEBOV was amplified using the primer set of each of the embodiments. The amplification of the Guinea 14 strain of ZEBOV was achieved, thereby detecting the ZEBOV with high accuracy.

For example, the use of Primer Set Nos. 20 to 23 allows for a rapid amplification of the Zaire 76 strain, in addition to the Guinea 14 strain of ZEBOV. Although it is not shown in the data, the use of Primer Set Nos. 20 to 23 allows for a rapid amplification of the Zaire 95 strain.

(5) Detection of Guinea 14 Strain of ZEBOV

The RT-LAMP reaction was performed in the same manner as in the paragraph (2) except that the amount of synthetic RNA used for the LAMP reaction was in the range of from $6.1 \times 10^5$ copies to $6.1 \times 10^1$ copies of Guinea 14 strain. The used primer sets include Set IDs 21 and 26. In these primer sets, only F3 primers are different from each other. Specifically, F3 primers in Set ID 21 and Set ID 26 include nucleotide sequences represented by SEQ ID NO: 39 and SEQ ID NO: 2, respectively. As other primers, primers including mutually identical sequences were used. Specific configurations of these used primer sets are shown in Table 4 and Table 6.

A 10-fold serial dilution of a stock solution was previously performed, thereby adjusting the concentration of Guinea 14 strain of ZEBOV in a sample to a range of from $10^{-5}$-fold ($3.05 \times 10^5$ copies/μL) to $10^{-9}$-fold ($3.05 \times 10^1$ copies/μL).

The test method was performed by the same method described in the paragraph of (2) Confirmation of Reactivity of Primer Set.

TABLE 6

| Set ID | Primer's name | Sequence information | Chain length | SEQ ID NO. |
|---|---|---|---|---|
| 26 | Tr273wa4_F3 | CAATAAACAACTATTTAAATAAC | 23 | 2 |
|  | Tr273wa_B3 | CTGGCAAGATATTGATACAACA | 22 | 10 |
|  | Tr273_FIP | GTCACACATGCTGCATTGTGttttCTATATTTAGCCTCTCTCCCT | 45 | 12 |
|  | Tr2_BIP | AACGCAACATAATAAACTCTGCAttttATCAATAACAATATGAGCCCAG | 49 | 13 |
|  | Tr273wa_LF | AATTTTTTGATTATCACGC | 19 | 11 |

Figure 7:
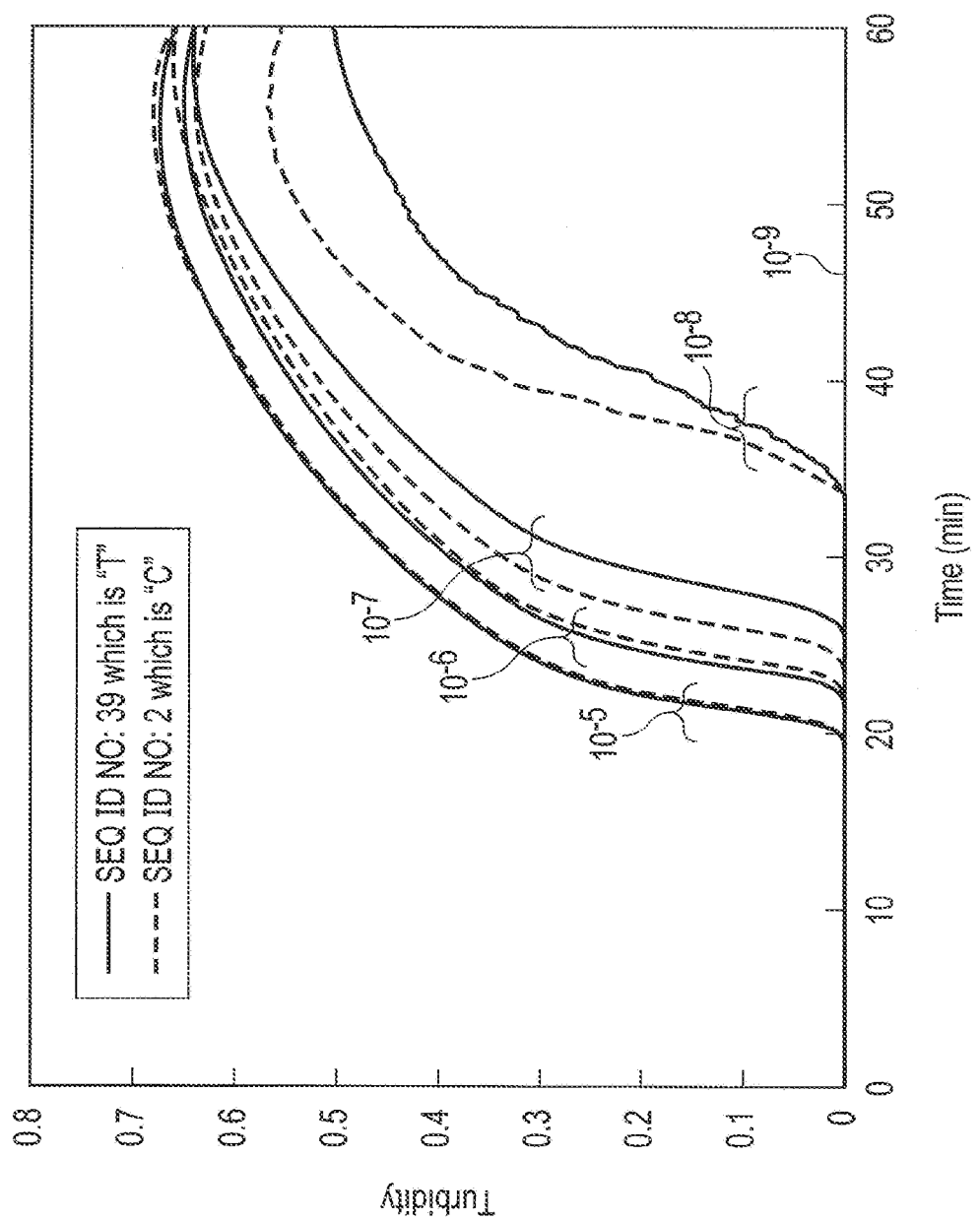
FIG. 7 is a graph showing the experimental results.

The results are shown in FIG. 7. FIG. 7 is a graph showing the results when viral genes were amplified by two types of LAPM primers. The turbidity was plotted on a vertical axis and the time (in minutes) was plotted on a horizontal axis. A difference between F3 primers respectively included in Set ID 21 and Set ID 26 is only the type of base at the position 8 from the 5' end. That is, the base at the position 8 from the 5' end is thymine (t or T) for Set ID 21, and cytosine (c or C) for Set ID 26.

In the cases of all the synthetic RNA concentrations, the use of both of Set ID 21 and Set ID 26 allowed for favorable amplification of a nucleic acid derived from the Guinea 14 strain of ZEBOV. In the case where the concentration of the virus was relatively low, for example, the $10^{-7}$-fold dilution ($6.1 \times 10^3$ copies) or $10^{-8}$-fold dilution ($6.1 \times 10^2$ copies), the tendency of high amplification efficiency was observed in the primer set of Set ID 26.

The above results show that the use of Set ID 21 and Set ID 26 allows a nucleic acid derived from the Guinea 14 strain of ZEBOV to be amplified almost equally, favorably, and specifically. This suggests that the use of the primer set of each of the embodiments allows for accurate and rapid detection.

(6) Clinical Detection of Guinea 14 Strain of ZEBOV

Similarly, as for the detectability of the Guinea 14 strain of ZEBOV in a sample extracted from Guinea, tests were performed to compare the RT-LAMP method using the primer set according to each of the embodiments to the Quantitative RT-PCR (qRT-PCR).

(a) RT-LAMP Method

The RT-LAMP method was performed using the instrument for isothermal nucleic acid amplification and real-time fluorescence detection (Genie (registered trademark) III (Optigene limited, West Sussex, U.K.)). DEPC-treated water and synthetic RNA of Zaire 76 strain were used as a negative control and a positive control, respectively.

The real-time fluorescence detection of LAMP amplification was performed in accordance with the protocol of the manufacturer of Isothermal Master Mix for Genie III (OptiGene Limited).

| Composition of LAMP reaction solution (25 μL) | |
|---|---|
| FIP | 20 pmol |
| BIP | 20 pmol |
| F3 | 5 pmol |
| B3 | 5 pmol |
| LF | 10 pmol |
| Isothermal Master Mix | 15.0 μL |
| AMV reverse transcriptase (0.15 U) | 1.0 μL |
| RNA sample | 5.0 μL. |

In the LAMP amplification and fluorescence detection, amplification was performed in Genie (registered trademark) III at 63° C. for 30 minutes, and then dissociation analysis was performed at 95° C. to 80° C. Nonspecific amplification was excluded by comparison with the melting temperature for the reaction of the positive control.

(b) RT-PCR Method

In the RT-PCR method, comparative tests were performed using the QuantiTect RT-PCR kit (QIAGEN), the Zaire EBOV 2014 primer, and the probe kit (TIM MOLBIOL, Hamburg, Germany). The TIB kit is a kit received an Emergency Use Authorization (EUA) for EBOV diagnosis from U.S. Food and Drug Administration.

An RNA sample (5 μL) was added to each reaction mixture (25 μL). Each reaction was performed in the Smart Cycler II system (Cepheid, U.S.A).

The test conditions of the RT-LAMP method and the qRT-PCR method are shown in Table 7.

TABLE 7

| Method | qRT-PCR | RT-LAMP |
|---|---|---|
| Instrument | Smart Cycler (Cepheid, USA) | GenieIII (OptiGene, UK) |
| Reagent | QuantiTect RT-PCR Kit (Qiagen)/ LightMix KIT EBOZ (TIB MOLBIOL) | Isothermal Master Mix (Nippon Gene) |
| Amp condition | 50° C., 5 min 95° C., 15 min 45 cycle 95° C., 5 s; 55° C., 50 s | Preheat: 42° C. Amp & Detection: 63° C., 30 min Melting: 95-80° C. |

The RT-LAMP test was conducted by the blind test in which the diagnostic results obtained by the RT-PCR method were concealed. After the end of the tests, both the test results were compared.

(c) Results

The samples used in the tests were samples extracted from subjects who were suspected to have been infected with the Guinea 14 strain of ZEBOV.

As shown in Table 8, in all the samples, the results obtained by the RT-LAMP method and the qRT-PCR method were consistent with diagnostic results. In other word, even if the RT-LAMP method was used, the Guinea 14 strain of ZEBOV in each sample could be detected with the same accuracy as the qRT-PCR method.

TABLE 8

| | | qRT-PCR | | |
| | | Pos | Neg | Total |
|---|---|---|---|---|
| LAMP | Pos | 47 | 0 | 47 |
| | Neg | 0 | 53 | 53 |
| | Total | 47 | 53 | 100 |

With respect to the tests for detecting four typical samples with different virus titers (clinical samples A, B, and C and D) by either the RT-LAMP method or the qRT-PCR method, the time required for detection of viral RNAs are shown in Table 9.

TABLE 9

| Clinical sample | qRT-PCR | | RT-LAMP |
|---|---|---|---|
| | CT | Time required for detection (min) | Time required for detection (min) |
| A | 22.2 | 40.3 | 10.2 |
| B | 25.2 | 43.1 | 12.4 |
| C | 30.1 | 47.6 | 13.0 |
| D | 37.1 | 54.0 | 13.3 |

As is clear from the results shown in Table 9, in the case of each of the clinical samples A, B, and C and D, the time required for detection by the RT-LAMP method was significantly shorter than the time required for detection by the qRT-PCR method. For example, the time required for detection by the RT-LAMP method was 10.2 minutes at the shortest and 13.3 minutes at the longest. As compared to this, the time required for detection by the qRT-PCR method was 40.3 minutes at the shortest and 54.0 minutes at the longest.

As described above, it is demonstrated that when the primer set of each of the embodiments is used, the ZEBOV strain including the Guinea 14 strain can be rapidly detected with high accuracy similar to that of the qRT-PCR method used as the conventional EBOV diagnosis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nucleic acid primer set for LAMP amplification that specifically amplifies a Zaire Ebola virus,
   wherein a template sequence to be amplified by the primer set includes an F3c sequence, an F2c sequence, an F1c sequence, a B1 sequence, a B2 sequence, and a B3 sequence from 3' side toward the 5' side in this order, the primer set includes an FIP primer, an F3 primer, a BIP primer, and a B3 primer, the FIP primer includes a F1c sequence and a F2 sequence from the 5' side toward the 3' side in this order, the F3 primer includes a F3 sequence, the BIP primer includes a B1c sequence and a B2 sequence from the 5' side toward the 3' side in this order, the B3 primer includes a B3 sequence,
   wherein F1 and F1c sequences are complementary to each other, F2 and F2c sequences are complementary to each other, F3 and F3c sequences are complementary to each other, B1 and the B1c sequences are complementary to each other, B2 and B2c sequences are complementary to each other, and B3 and B3c sequences are complementary to each other, and
   wherein the F1 sequence includes at least 13 consecutive bases included in SEQ ID NO: 31 or 64 or complementary sequences of the bases,
   the F2 sequence includes at least 13 consecutive bases included in SEQ ID NO: 62 or 63 or complementary sequences of the bases,
   the F3 sequence includes at least 13 consecutive bases included in SEQ ID NO: 29, 36, 38, 55, 56, 57, 58, 59, 60 or 61 or complementary sequences of the bases,
   the B1c sequence includes at least 13 consecutive bases included in SEQ ID NO: 68, 69, 70, 71, 72, 73, 74 or 75 or complementary sequences of the bases,
   the B2c sequence includes at least 13 consecutive bases included in SEQ ID NO: 65 or 66 or complementary sequences of the bases, and
   the B3c sequence includes at least 13 consecutive bases included in SEQ ID NO: 34, 67, 82 or 83 or complementary sequences of the bases.

2. The primer set of claim 1,
   wherein the F3 primer is at least 13 consecutive bases so as to include consecutive bases from any of the bases at positions 1-5 from the 5' end which are included in SEQ ID NO: 29, 55, 60 or 61, or complementary sequences of the bases,
   the FIP primer includes a sequence represented by SEQ ID NO: 4, 44 or 45 or complementary sequences of the sequences and includes and includes a sequence represented by SEQ ID NO: 3 or 42 or complementary sequences of the sequences, the B1c sequence in the BIP primer is at least 13 consecutive bases so as to include any of the bases at positions 1-5 from the 5' end which are included in SEQ ID NO: 75 or complementary sequences of the bases, or at least 13 consecutive bases so as to include any of the bases at positions 1-6 from the 3' end or complementary sequences of the bases, the B2c sequence is at least 13 consecutive bases so as to include any of the bases at positions 1-7 from the 5' end which are included in SEQ ID NO: 65 or 66 or complementary sequences of the bases, the B3 primer is at least 13 consecutive bases so as to include any of the bases at positions 1-5 from the 5' end which is included in SEQ ID NO: 82 or complementary sequences of the bases, or at least 13 consecutive bases so as to include any of the bases at positions 1-7 from the 3' end which is included in SEQ ID NO: 34 or complementary sequences of the bases, and the LFc primer includes a sequence represented by SEQ ID NO: 11.

3. The primer set of claim 1,
wherein the F3 primer includes a sequence represented by any of SEQ ID NO: 2, 17, 20, 22, and 39 or a complementary sequence of the sequence,
the FIP primer includes a sequence represented by any of SEQ ID NO: 12, 18, and 21 or a complementary sequence of the sequence,
the BIP primer includes a sequence represented by any of SEQ ID NO: 13, 23, 24, 25, 26, and 27 or a complementary sequence of the sequence, and
the B3 primer includes a sequence represented by either SEQ ID NO: 10 or 19 or a complementary sequence of the sequence.

4. The primer set of claim 1,
wherein the F3 primer includes at least 13 consecutive bases which are included in a sequence represented by any of SEQ ID NOS: 2, 17, 20, 22, and 39 or a complementary sequence of the sequence,
the FIP primer includes at least 13 consecutive bases which are included in a sequence represented by any of SEQ ID NOS: 12, 18, and 21 or a complementary sequence of the sequence,
the BIP primer includes at least 13 consecutive bases which are included in a sequence represented by any of SEQ ID NOS: 13, 23, 24, 25, 26, and 27 or a complementary sequence of the sequence, and
the B3 primer includes at least 13 consecutive bases which are included in a sequence represented by either SEQ ID NO: 10 or 19 or a complementary sequence of the sequence.

5. The primer set of claim 1,
wherein each combination of recognition sequences for the F3, FIP, BIP, and B3 primers included in the primer set is selected from the group consisting of the followings (1) to (19):
(1) a combination of SEQ ID NOS: 17, 18, 13, and 19;
(2) a combination of SEQ ID NOS: 22, 21, 15, and 10;
(3) a combination of SEQ ID NOS: 20, 21, 23, and 10;
(4) a combination of SEQ ID NOS: 22, 21, 24, and 10;
(5) a combination of SEQ ID NOS: 22, 21, 25, and 10;
(6) a combination of SEQ ID NOS: 22, 21, 26, and 10;
(7) a combination of SEQ ID NOS: 22, 21, 27, and 10;
(8) a combination of SEQ ID NOS: 20, 12, 23, and 10;
(9) a combination of SEQ ID NOS: 20, 12, 24, and 10;
(10) a combination of SEQ ID NOS: 20, 12, 25, and 10;
(11) a combination of SEQ ID NOS: 20, 12, 26, and 10;
(12) a combination of SEQ ID NOS: 20, 12, 27, and 9;
(13) a combination of SEQ ID NOS: 20, 12, 13, and 9;
(14) a combination of SEQ ID NOS: 20, 12, 13, and 19;
(15) a combination of SEQ ID NOS: 22, 12, 13, and 10;
(16) a combination of SEQ ID NOS: 22, 12, 13, and 19;
(17) a combination of SEQ ID NOS: 39, 12, 13, and 10;
(18) a combination of SEQ ID NOS: 2, 12, 13, and 10; and
(19) a combination of complementary sequences of four sequences included in the combinations (1) to (18).

6. The primer set of claim 1, wherein the Zaire Ebola virus is Guinea 14 strain.

7. The primer set of claim 1, wherein the Zaire Ebola virus is Guinea 14 strain, Zaire 76 strain or Zaire 95 strain.

8. The primer set of claim 1,
wherein the FIP primer further includes a linker between the F1c sequence and the F2 sequence and/or the BIP primer includes a linker between the B1 sequence and the B2c sequence.

9. The primer set of claim 8, wherein the linker is formed of an arbitrary base sequence having a base length of 1 to 50.

10. The primer set of claim 1, further comprising an LFc primer that includes a sequence represented by SEQ ID NO: 11 or a complementary sequence of the sequence.

11. An assay kit for detecting Zaire Ebola virus comprising:
a primer set of claim 1; and
a container that accommodates the primer set.

12. The assay kit of claim 11, wherein the Zaire Ebola virus is Guinea 14 strain.

13. The assay kit of claim 11, wherein the Zaire Ebola virus is Zaire 76 strain, Zaire 95 strain or Guinea 14 strain.

14. A nucleic acid structure comprising:
a first stern-loop structure which includes an F1 sequence, an F2c sequence, and an F1c sequence from the 3' side toward the 5' side in this order and in which the F1 sequence is bound to the F1c sequence to form a double-strand;
a second stem-loop structure which includes an B1 sequence, an B2 sequence, and an B1c sequence from the 3' side toward the 5' side in this order and in which the B1 sequence is bound to the B1c sequence to form a double-strand;
a third stem-loop structure which includes an F1c sequence, an F2 sequence, and an F1 sequence from the 5' side toward the 3' side in this order and in which the F1c sequence is bound to the F1 sequence to form a double-strand;
a fourth stem-loop structure which includes a B1c sequence, a B2c sequence, and a B1 sequence from the 5' side toward the 3' side in this order and in which the B1c sequence is bound to the B1 sequence to form a double-strand;
a first dumbbell structure which includes an F1 sequence, an F2c sequence, an F1c sequence, a B1 sequence, a B2 sequence, and a B1c sequence from the 3' side toward the 5' side in this order and in which the F1 sequence is bound to the F1c sequence to form a double-strand, the B1 sequence is bound to the B1c sequence to form a double-strand; and/or
a second dumbbell structure which includes an F1c sequence, an F2 sequence, an F1 sequence, a B1c sequence, a B2c sequence, and a B1 sequence from the 3' side toward the 5' side in this order and in which the F1c sequence is bound to the F1 sequence to form a double-strand, the B1c sequence is bound to the B1 sequence to form a double-strand;

wherein F1 and F1c sequences are complementary to each other, F2 and F2c sequences are complementary to each other, F3 and F3c sequences are complementary to each other, B1 and B1c sequences are complementary to each other, B2 and B2c sequences are complementary to each other, and B3 and B3c sequences are complementary to each other, and wherein the F1 sequence includes at least 13 consecutive bases included in SEQ ID NO: 31 or 64 or complementary sequences of the bases, the F2 sequence includes at least 13 consecutive bases included in SEQ ID NO: 62 or 63 or complementary sequences of the bases, the F3 sequence includes at least 13 consecutive bases included in SEQ ID NO: 29, 36, 38, 55, 56, 57, 58, 59, 60 or 61 or complementary sequences of the bases, the B1c sequence includes at least 13 consecutive bases included in SEQ ID NO: 68, 69, 70, 71, 72, 73, 74 or 75 or complementary sequences of the bases, the B2c sequence includes at least 13 consecutive bases included in SEQ ID NO: 65 or 66 or complementary sequences of the bases, and the B3c sequence includes at least 13 consecutive bases included in SEQ ID NO: 34, 67, 82, or 83 or complementary sequences of the bases.

15. The nucleic acid structure of claim 14, wherein the nucleic acid structure is derived from Guinea 14 strain of Zaire Ebola virus as a template.

16. The nucleic acid structure of claim 15, wherein the Zaire Ebola virus is Guinea 14 strain, Zaire 76 strain or Zaire 95 strain.

17. A method of detecting Zaire Ebola virus, comprising:

amplifying a nucleic acid included in a specimen using the primer set of claim 1; and determining whether the Zaire Ebola virus is included in the specimen according to turbidity or fluorescence.

18. The method of claim 17, wherein the Zaire Ebola virus is Guinea 14 strain.

19. The method of claim 17, wherein the Zaire Ebola virus is Guinea 14 strain, Zaire 76 strain or Zaire 95 strain.

* * * * *